(12) United States Patent
Aikawa et al.

(10) Patent No.: US 8,976,242 B2
(45) Date of Patent: Mar. 10, 2015

(54) VISUAL INSPECTION APPARATUS AND VISUAL INSPECTION METHOD

(75) Inventors: Tetsuro Aikawa, Yokohama (JP); Yoshinori Satoh, Kawasaki (JP); Makoto Ochiai, Yokohama (JP); Tatsuya Oodake, Zushi (JP); Hiroyuki Adachi, Shinagawa-ku (JP); Yasuhiro Yuguchi, Yokohama (JP); Junichi Takabayashi, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 786 days.

(21) Appl. No.: 12/681,625

(22) PCT Filed: Oct. 1, 2008

(86) PCT No.: PCT/JP2008/067860
§ 371 (c)(1),
(2), (4) Date: Jun. 1, 2010

(87) PCT Pub. No.: WO2009/044785
PCT Pub. Date: Apr. 9, 2009

(65) Prior Publication Data
US 2010/0283847 A1 Nov. 11, 2010

(30) Foreign Application Priority Data

Oct. 3, 2007 (JP) .............................. P2007-259481
May 13, 2008 (JP) .............................. P2008-126321
May 28, 2008 (JP) .............................. P2008-139561

(51) Int. Cl.
*H04N 7/18* (2006.01)
*G21C 17/003* (2006.01)
(Continued)

(52) U.S. Cl.
CPC .......... *G21C 17/003* (2013.01); *G01N 21/8803* (2013.01); *G01N 21/8851* (2013.01); *G06T 3/4069* (2013.01); *G06T 7/0004* (2013.01); *G21C 17/08* (2013.01); *G21F 7/02* (2013.01)
USPC ........................................................ 348/142

(58) Field of Classification Search
USPC ............................................................ 348/82
See application file for complete search history.

(56) References Cited

U.S. PATENT DOCUMENTS 6,831,995 B1    12/2004  Asano et al.
7,916,971 B2 *  3/2011   Bigioi et al. .................. 382/275
(Continued)

FOREIGN PATENT DOCUMENTS

EP    1 492 051 A2    12/2004
JP    4 90284         3/1992
(Continued)

OTHER PUBLICATIONS

Extended European Search Report issued Nov. 4, 2011, in Patent Application No. 08836688.5.
(Continued)

*Primary Examiner* — Dave Czekaj
*Assistant Examiner* — Tracy Li
(74) *Attorney, Agent, or Firm* — Oblon, McClelland, Maier & Neustadt, L.L.P.

(57) ABSTRACT

The present invention includes a camera which takes an image of a camera or an inspection target; a device which estimates the movement of the inspection target; a device which generates a high resolution image having a higher resolution than the pixel resolution of a video image taken by the camera from the video image taken by the camera; a device which evaluates the quality of the high resolution image generated by the generation device; and a device which presents an inspector who visually inspects the inspection target with the high resolution image together with the quality evaluation result of the high resolution image. The present invention can improve the reliability of inspection by use of the high resolution image as well as can reduce the inspection time, and further can guarantee the reliability of the inspection using a high resolution image.

6 Claims, 23 Drawing Sheets

(51) Int. Cl.
*G01N 21/88* (2006.01)
*G06T 3/40* (2006.01)
*G06T 7/00* (2006.01)
*G21C 17/08* (2006.01)
*G21F 7/02* (2006.01)

(56) References Cited

U.S. PATENT DOCUMENTS

| | | | |
|---|---|---|---|
| 2001/0033683 A1* | 10/2001 | Tanaka et al. | 382/149 |
| 2003/0032436 A1 | 2/2003 | Mikuni | |
| 2003/0137585 A1 | 7/2003 | Mahon et al. | |
| 2005/0242286 A1* | 11/2005 | Watanabe et al. | 250/310 |
| 2006/0114531 A1 | 6/2006 | Webb et al. | |
| 2007/0019887 A1* | 1/2007 | Nestares et al. | 382/299 |
| 2007/0053022 A1* | 3/2007 | Misaka | 358/518 |
| 2007/0187571 A1* | 8/2007 | Ebe et al. | 250/201.2 |
| 2008/0309780 A1* | 12/2008 | Kanamori et al. | 348/222.1 |

FOREIGN PATENT DOCUMENTS

| | | |
|---|---|---|
| JP | 6 18240 | 1/1994 |
| JP | 7 37065 | 2/1995 |
| JP | 10 117304 | 5/1998 |
| JP | 2000 338000 | 12/2000 |
| JP | 2001 148019 | 5/2001 |
| JP | 2003 121195 | 4/2003 |
| JP | 2006 78328 | 3/2006 |
| JP | 2007 118541 | 4/2007 |
| JP | 3972647 | 6/2007 |
| JP | 2007 333639 | 12/2007 |

OTHER PUBLICATIONS

James Micheal Reed, et al., "Subpixel Parameter Estimation for Elliptical Shapes Using Image Sequences", Proceedings of the 1994 IEEE International Conference on Multisensor Fusion and Integration for Intelligent Systems, XP010137947, Oct. 2-5, 1994, pp. 567-574.

Lijun Yin, et al., "Hyper-Resolution: Image detail reconstruction through parametric edges", Computers and Graphics, Elsevier, vol. 29, No. 6, XP025272314, Dec. 1, 2005, pp. 946-960.

Office Action issued Sep. 2, 2014 in European Patent Application No. 08836688.5.

Zhao, Wen-Yi, "Super-Resolution With Significant Illumination Change", Proc. International Conference on Image Processing (ICIP 2004), vol. 3, pp. 1771-1774, 2004.

\* cited by examiner

COMPARISON OF BRIGHTNESS DISPERSION

SAME RESOLUTION:COMPARISON

VISUAL INSPECTION APPARATUS AND VISUAL INSPECTION METHOD

TECHNICAL FIELD

The present invention relates to apparatus and method for using by an inspector to visually inspect an inspection target, and particularly to apparatus and method for visual inspection of a plant structure.

BACKGROUND ART

Power plants or industrial plants perform periodical inspections in order to maintain the safety and reliability of equipment. In particular, visual inspections (VT) are frequently used for ease of inspection. For example, the visual inspections have been frequently used where in a nuclear power plant, a remotely-operated camera is used to take an image of an inspection target and the image is displayed on a monitor so that an inspector can visually confirm the image (Patent Document 1). The purpose of the method is to suppress the number of people (workers and inspectors) working in a radiation control area of the nuclear power plant and to shorten the working hours thereof.

Further, there has been invented a method of obtaining a wide range of image data by scanning images inside a wide range of a large facility such as a nuclear power plant using an inspection apparatus mounting a plurality of cameras (Patent Document 2).

Furthermore, the present inventors have developed and disclosed a shroud automatic inspection apparatus which automatically detects a shroud defect inside a nuclear pressure vessel (Patent Document 3). The shroud automatic inspection apparatus is configured such that a sensing device moves above a shroud surface to take an image and the image is inputted to an image processing device; the image processing device performs image processing on a picture signal from the sensing device; if the shroud is assumed to have a defect, the image processing device calculates the 3D (three-dimensional) shape of that portion; and a flaw detector further calculates the detailed three-dimensional shape of the defect. The shroud automatic inspection apparatus can automatically detect any defect from the continuously fed shroud images and can detect a more detailed three-dimensional shape of the detected defect portion.

Patent Document 1 is Japanese Published Unexamined Patent Application (Patent Laid-Open) No. 2000-346976 (JP-A-2000-346976);

Patent Document 2 is Japanese Published Unexamined Patent Application (Patent Laid-Open) No. 2002-149859 (JP-A-2002-149859); and Patent Document 3 is Published Unexamined Patent Application (Patent Laid-Open) No. 11-326580 (JP-A-11-326580).

DISCLOSURE OF THE INVENTION

The aforementioned visual inspection requires an inspector to visually detect a defect from camera images. Thus, if the camera resolution is not enough to detect a defect, defect visibility is reduced, leading to a possibility of failing to detect a defect by oversight. In order to prevent such a defect oversight, an inspection needs to be performed by narrowing the field of view, but unfortunately, it takes time to take images of all the structures inside a furnace of a large facility using a camera with a narrow field of view, and thus the inspection time becomes longer.

Further, as disclosed in Patent Document 2, there has been known technique of reducing the inspection time using a plurality of cameras, but unfortunately the method requires a larger apparatus, higher costs and lower operability. In addition, as the known technique as disclosed in Patent Document 2 merely obtain images does not exceed the resolution of each camera used, for user, the obtained images are not always sufficient resolution.

Alternatively, there is a method of using a high-resolution camera, but the high-resolution camera has a low frame rate, and thus time difference occurs between the time when the operator operates the camera and the time when the operation is reflected on the camera image, leading to a low operability. Further, when a high-resolution camera is used, there is an inconvenience in that it takes time to take images of all the structures inside a furnace of the large facility using a camera with a narrow field of view, and thus the inspection time becomes longer. Furthermore, a high-resolution image has a large data size, and thus there is an inconvenience in that the recording apparatus requires a larger capacity than before, and it takes more time to transmit data through a communication line.

Further, with regards to the resource of inspectors, currently, inspectors perform on-site inspections and thus it is impossible for the same inspector to perform inspections on different power plants. Therefore, it is difficult to fully utilize the resource of inspectors.

The present invention has been made to eliminate the above inconveniences, and an object of the present invention is to provide low-cost and compact apparatus and method, for visual inspection, capable of improving inspection quality using a camera having an ordinary resolution by presenting inspectors with inspection images having excellent visibility of defects.

Another object of the present invention is to provide visual inspection apparatus and visual inspection method allowing the same inspector to inspect different power plants without a need to be on site and thus capable of fully utilizing the resource of inspectors.

Still another object of the present invention is to provide visual inspection apparatus and visual inspection method using a camera having an ordinary resolution to obtain an image (high resolution image) having a higher resolution than the ordinary resolution so as to enable inspection using the high resolution image and thus capable of improving reliability of inspection and reducing the inspection time.

A visual inspection apparatus according to the present invention comprising:

an image input device which feeds a video image of an inspection target and outputs a digital data image;

an image selection device which selects an inspection image to be used for inspection based on a feature quantity of images outputted from the image input device;

a high resolution image creation device which generates a high resolution image having a higher resolution than the resolution of the inspection image from the inspection image; and an image output device which displays the inspection image and the high resolution image.

A visual inspection method according to the present invention comprising the steps of:

feeding an inspection video image and outputting a digital image as the inspection video image;

selecting an inspection image to be used for inspection based on a feature quantity of the output images;

generating a high resolution image having a higher resolution than the resolution of the inspection image; and presenting an inspector who visually inspects the inspection target by displaying the inspection target on a monitor with the inspection image and the high resolution image.

The visual inspection apparatus and the visual inspection method according to the present invention can provide a low-cost and compact inspection apparatus and inspection method capable of improving inspection quality by presenting inspectors with inspection images having excellent visibility of defects using a camera having an ordinary resolution as well as can provide inspection apparatus and inspection method allowing the same inspector to inspect different power plants without a need to be on site.

Further, the time-series images of an inspection target taken by a camera are used to generate high resolution images each having a higher pixel resolution than the pixel resolution of the camera images by software and to present the inspector with the high resolution images so that the inspector can use the high resolution images to visually inspect the inspection target, thereby allowing improved reliability of inspection and reduction in inspection time. Furthermore, the quality of the obtained high resolution images is quantitatively evaluated and presented to the inspector, thereby guaranteeing the reliability of inspection using high resolution images.

BRIEF DESCRIPTION OF THE DRAWINGS

FIG. 5 (which includes FIGS. 5A and 5B) is an explanatory drawing explaining the high resolution image generation methods applied to the high resolution image creation device of the visual inspection apparatus according to the first embodiment of the present invention.

FIG. 17 (which includes FIGS. 17A and 17B) is an explanatory drawing explaining the block matching performed by the movement estimation device.

FIG. 19 (which includes FIGS. 19A and 19B) is an explanatory drawing explaining a first image evaluation method applied to the image evaluation device.

FIG. 20 (which includes FIGS. 20A, 20B and 20C) is an explanatory drawing explaining a second image evaluation method of evaluating a high resolution image performed by the image evaluation device.

BEST MODE FOR CARRYING OUT THE INVENTION

Hereinafter, the best mode for carrying out the present invention will be described by referring to the accompanying drawings. It should be noted that the present invention is not limited to the embodiments. That is, the present invention includes embodiments which are executed by deleting several components from all the components disclosed in each embodiment or by appropriately mixing several components each disclosed in a different embodiment.

First Embodiment

Figure 1:
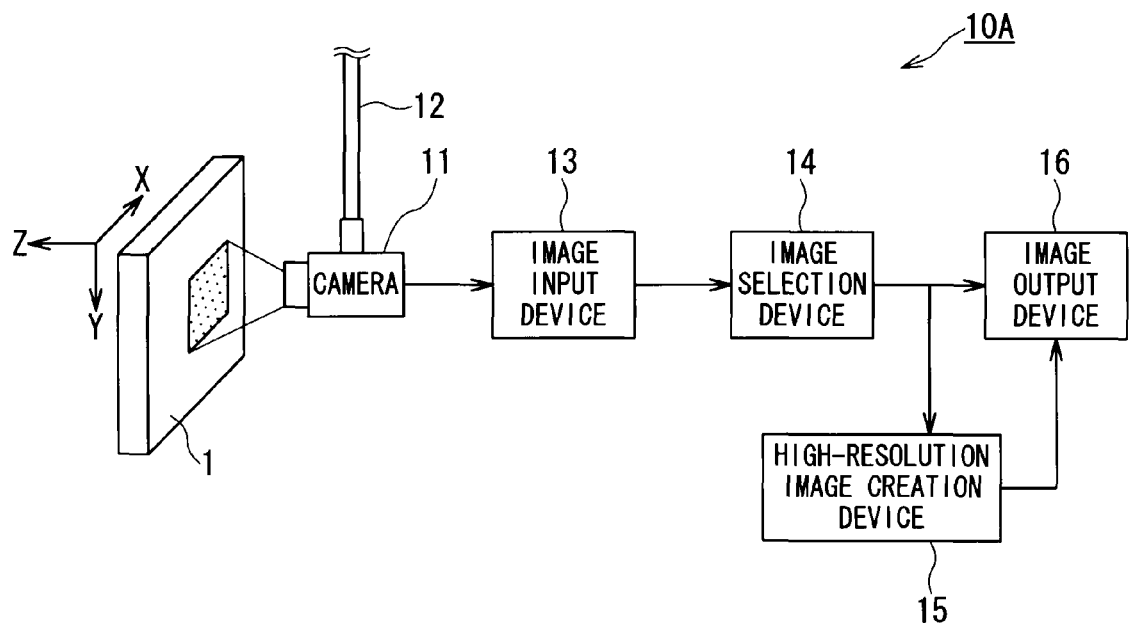
FIG. 1 is a block diagram illustrating a configuration of a visual inspection apparatus according to a first embodiment of the present invention.

FIG. 1 is a block diagram illustrating a configuration of a visual inspection apparatus (which will be referred to as "first visual inspection apparatus", hereinafter) 10A according to a first embodiment of the present invention.

As illustrated in FIG. 1, the first visual inspection apparatus 10A includes a camera 11 which takes an image of an inspection target (object to be inspected) 1; a supporting device 12 which supports the camera 11; an image input device 13 which feeds a video image taken by the camera 11 and generates a digital image; an image selection device 14 which selects an inspection image to be used for inspection based on the feature quantity from inspection images outputted from the image input device 13; a high resolution image creation device 15 which uses the image selected by the image selection device 14 to generate a high resolution image having a higher resolution than the resolution of the selected image; and an image output device 16 which displays the inspection image selected by the image selection device 14 and the high resolution image generated by the high resolution image creation device 15.

Now, the operation of the first visual inspection apparatus 10A will be described.

The camera 11 can move horizontally and vertically with respect to the inspection target 1 in accordance with the movement or operation of the supporting device 12 to scan and can take an image of the inspection target 1. The image taken by the camera 11 is outputted from the camera 11 to the image input device 13.

The supporting device 12 hangs the camera 11, for example, as illustrated in FIG. 1, so as to hold the camera 11 at a predetermined position capable of taking an image of inspection target 1. Further, the supporting device 12 includes a drive mechanism for adjusting the position of the camera 11 so as to enable a manual or automatic adjustment of the position of the camera 11.

The image input device 13 inputs an image from the camera 11, performs digital conversion on the inputted image and outputs the converted digital image to the image selection device 14.

The image selection device 14 inputs the image (digital image) from the image input device 13, performs image processing on the inputted image to measure the image feature quantity, uses the measured image feature quantity to select an image (inspection image) to be used for inspection, and outputs the selected image to both the high resolution image creation device 15 and the image output device 16.

The high resolution image creation device 15 generates (creates) a high resolution image having a higher resolution than that of the original image by utilizing a plurality of inspection images inputted from the image selection device 14 and outputs the high resolution image to the image output device 16.

The image output device 16 displays the inspection image received from the image selection device 14 and the high resolution image received from the high resolution image creation device 15 to be provided to the inspector. Then, the inspector can appropriately compare both images to visually find and detect any defect in a quick and accurate manner as well as can evaluate the generated high resolution image. Then, based on the evaluation, the inspector can give an instruction to take an image of the inspection target again and to perform the image processing again as needed.

The image selection methods (image processing) applied when the image selection device 14 selects the inspection image will be described in more detail.

Figure 2:
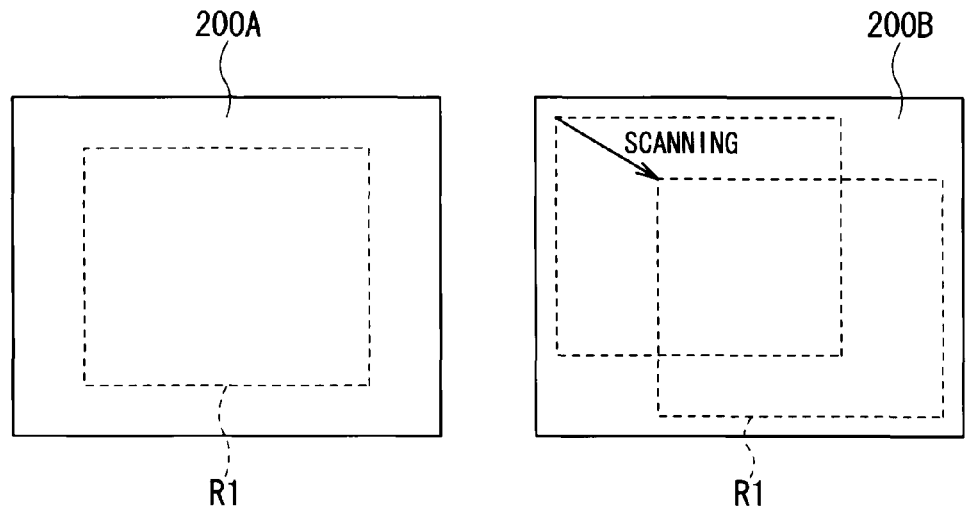
FIG. 2 is an explanatory drawing explaining a first image selection method applied to the image selection device of the visual inspection apparatus according to the first embodiment of the present invention.
Figure 3:
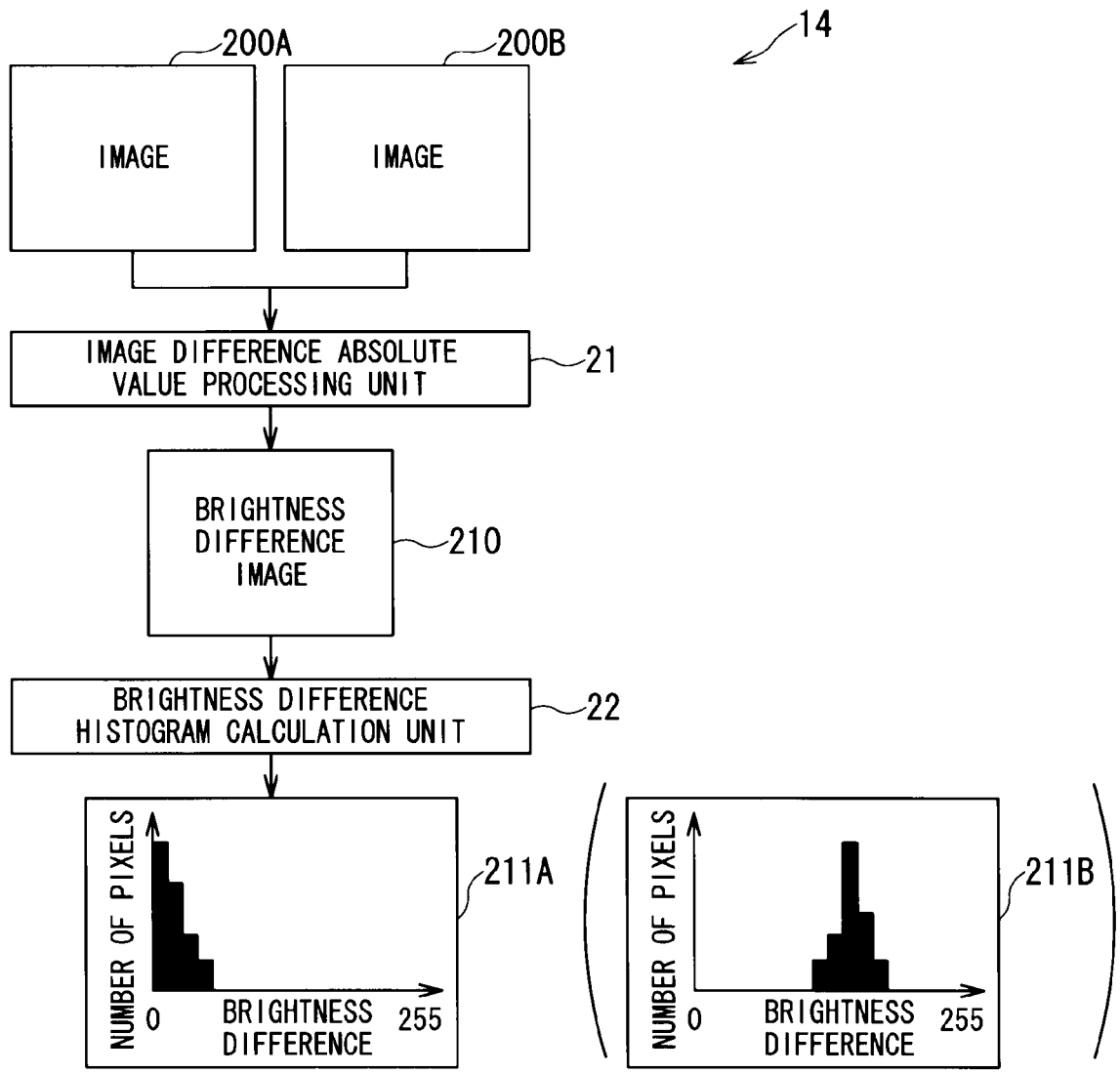
FIG. 3 is an explanatory drawing explaining a second image selection method applied to the image selection device of the visual inspection apparatus according to the first embodiment of the present invention.

FIGS. 2 and 3 are explanatory drawings explaining about the image selection methods applied when the image selection device 14 selects the inspection image, FIG. 2 is an explanatory drawing explaining a first image selection method and FIG. 3 is an explanatory drawing explaining a second image selection method. By referring to FIGS. 2 and 3, the first image selection method and the second image selection method will be described.

(First Image Selection Method)

The first image selection method is to search the correlation values of image brightness for a position having the highest correlation value and select an inspection image based on the shift amount per unit of time between the images with respect to the position.

FIG. 2 illustrates two images 200A and 200B which are inputted from the image input device 13. The image selection device 14 sequentially stores digital images inputted from the image input device 13, and performs image processing using the two images: the already stored image 200A and a new image 200B inputted from the image input device 13.

According to the first image selection method, the image selection device 14 sets a rectangular comparison region R1 to the image 200A and performs image scanning on the comparison region R1 by sequentially shifting the superimposed position of the images in units of pixels from the upper left to the lower right of the image 200B (indicated by the arrow in FIG. 2), executes matching at each position, and calculates the brightness correlation value.

The image selection device 14 searches the brightness correlation values calculated at each position for a position having the highest correlation value and calculates the shift amount between the images with respect to the position of the comparison region R1 of the image 200A. The shift amount obtained from this calculation indicates the amount of movement of FOV (field of view) according to the movement of the camera 11. Then, the image selection device 14 uses the difference in time to take images of the two images 200A and 200B to calculate the shift amount per unit of time therebetween. A large shift amount indicates a large camera movement and thus indicates a strong possibility that an image blur occurs. Therefore, the image selection device 14 selects an image having a small shift amount as the inspection image to be outputted.

It should be noted that the above description of the comparison region R1 has focused on a single rectangular shape, but the comparison region R1 may be of any shape so as to match the shape of the inspection target and block matching may be used for each of the plurality of local regions so as to correspond to a concave-convex shape of the surface thereof.

(Second Image Selection Method)

The second image selection method is to select an inspection image based on the histograms of brightness difference 211A and 211B obtained from a brightness difference image 210 indicating the brightness difference between the two images 200A and 200B.

As illustrated in FIG. 3, the image selection device 14 which performs the second image selection method includes: an image difference absolute value processing unit 21 which uses the two images 200A and 200B inputted from the image input device 13 to obtain the brightness difference image 210 indicating the brightness difference between the two images 200A and 200B; and a brightness difference histogram calculation unit 22 which uses the obtained brightness difference image 210 to obtain the brightness difference histograms 211 (211A and 211B). The image selection device 14 which performs the second image selection method works in the same manner as the image selection device 14 which performs the first image selection method. More specifically, the image selection device 14 sequentially stores images inputted from the image input device 13, and performs image processing using the two images: the already stored image 200A and a new image 200B inputted from the image input device 13.

According to the second image selection method, first, the image difference absolute value processing unit 21 performs the image difference absolute value processing on the inputted two images 200A and 200B to obtain the brightness difference image 210 indicating the brightness difference between the two images. Then, the brightness difference histogram calculation unit 22 uses the obtained brightness difference image 210 between two images to calculate the brightness difference histograms 211. Here, the brightness difference histograms 211 each are a frequency graph in which the brightness difference is plotted on the horizontal axis (in FIG. 3, 8 bits=0 to 255) and the number of pixels of each brightness difference is plotted on the vertical axis.

With reference to the brightness difference histogram 211, in the event that the brightness difference between the two images is small, the pixels are distributed on a side of smaller brightness difference as illustrated in the brightness difference histogram 211A. Further, in the event that the brightness difference between the images is large, the pixels are distributed on a side of larger brightness difference as illustrated in the brightness difference histogram 211B. The brightness difference between the images is caused by the change in lighting. The brightness difference histogram 211A indicates a small change in lighting; and the brightness difference histogram 211B indicates a large change in lighting. Thus, the image selection device 14 selects and outputs an image, of a histogram in which the frequencies of pixels are distributed on a side of smaller brightness difference, as an inspection image.

It should be noted that the present description has focused on a method of calculating absolute values of the image difference on the entire image, but calculating absolute values of the image difference may be performed on any region so as to suit the shape of inspection target 1 or may be performed on each local region so as to detect a local change in brightness.

Moreover, the present description has focused on the image selection methods by the image selection device 14 such that the first method is to select an image based on the movement of the camera; and the second method is to select an image based on the change in lighting, but the first method and the second method may be combined to select an image.

The high resolution image generation methods (image processing) applied when the high resolution image creation device 15 generates the high resolution image will be described in more detail.

Figure 4:
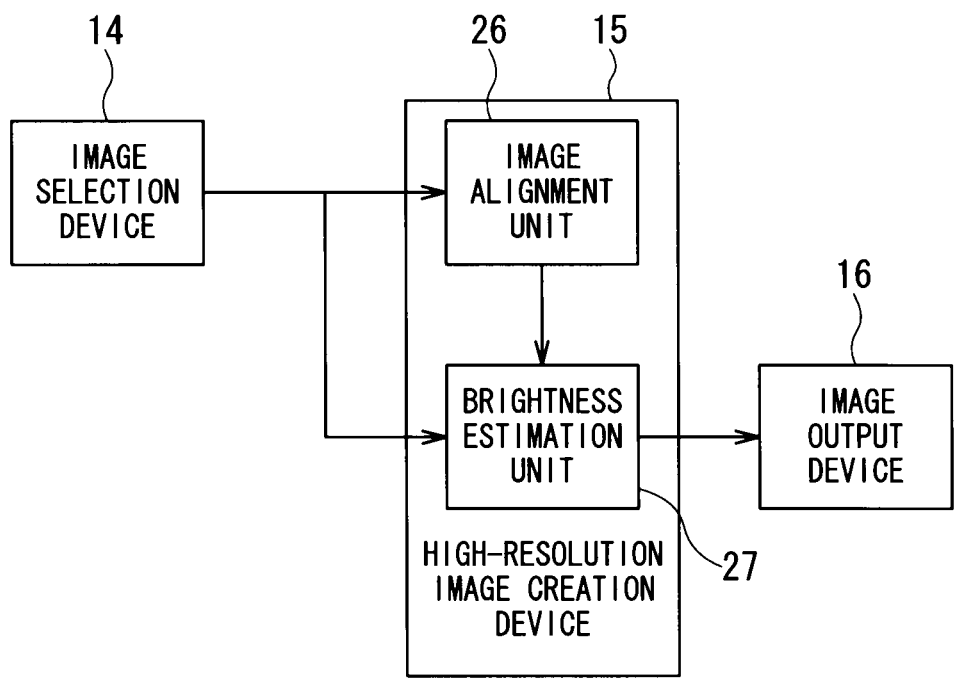
FIG. 4 is a schematic view illustrating a configuration of the high resolution image creation device of the visual inspection apparatus according to the first embodiment of the present invention.

FIG. 4 is a schematic view illustrating a configuration of the high resolution image creation device 15 of the first visual inspection apparatus 10A.

As illustrated in FIG. 4, the high resolution image creation device 15 includes an image alignment unit 26 and a brightness estimation unit 27. Each image selected by the image selection device 14 is inputted from the image selection device 14 to the image alignment unit 26 and the brightness estimation unit 27 of the high resolution image creation device 15.

The image alignment unit 26 sequentially stores inspection images inputted from the image selection device 14, and performs image processing on the two images: the already stored image and a new inspection image inputted from the image selection device 14 to compare the two images and perform image alignment at sub-pixel accuracy, namely, an accuracy of higher resolution than the resolution of a pixel.

The execution method is such that an image is enlarged to increase the pixel accuracy of the image; in the same manner as in the first image selection method of the image selection device 14, a comparison region is set, and the image is scanned by sequentially shifting the image alignment position in units of pixels; and matching is performed at each position to calculate the brightness correlation value. Then, the brightness correlation values calculated at each position are searched for a position having the highest correlation value to perform the image alignment. If the surface of the inspection target 1 is of a concave-convex shape, the distance from the camera 11 to the inspection target 1 is not constant, and thus the image alignment position is different for each local region. In that case, the matching is performed for each local region and the image alignment is performed for each local region.

The brightness estimation unit 27 uses the inspection image inputted from the image selection device 14 and the alignment position set by the image alignment unit 26 to generate an image (high resolution image) having a higher resolution than the resolution of the inspection image inputted from the image selection device 14.

Figure 5A:
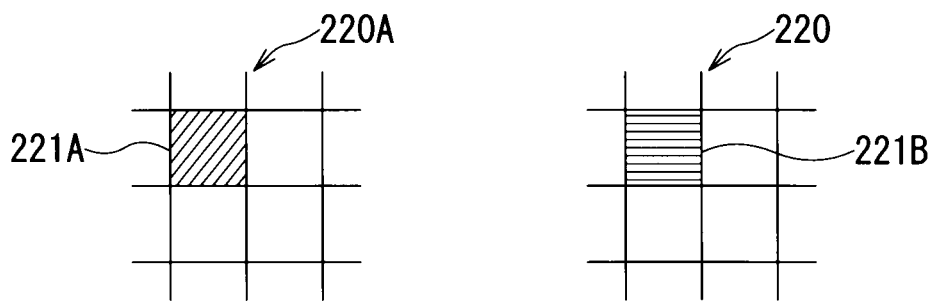
FIG. 5A is a schematic view illustrating the inspection images before a high resolution image is generated.
Figure 5B:
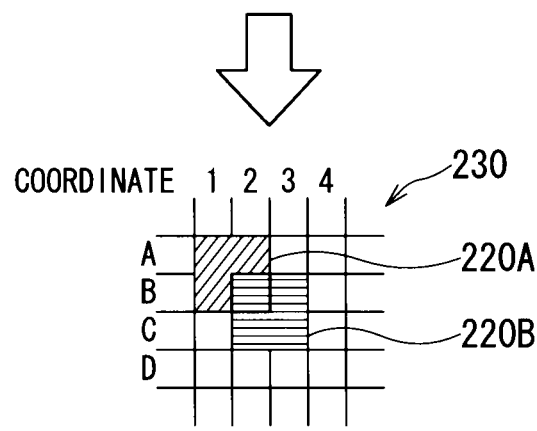
FIG. 5B is a schematic view illustrating the generated high resolution image.

FIG. 5 each are an explanatory drawing explaining the high resolution image generation methods (image processing) applied to the high resolution image creation device 15 of the first visual inspection apparatus 10A. FIG. 5A is a schematic view illustrating the inspection images 220A and 220B before a high resolution image is generated. FIG. 5B is a schematic view illustrating the generated high resolution image 230. Note that in FIG. 5, as an example, the resolution of the high resolution image 230 doubles the resolution of inspection images 220A and 220B.

The high resolution image creation device 15 performs image processing so as to obtain a high resolution image 230 illustrated in FIG. 5B on the basis of the inspection images 220A and 220B inputted from the image selection device 14 illustrated in FIG. 5A.

Assuming that a pixel 221A of the image 220A has coordinates (1, A), (2, A), (1, B), and (2, B) of an high resolution image 230 as illustrated in FIG. 5B, a pixel 221B of the image 220B is calculated from the alignment position set by the image alignment unit 26 to find the coordinates of the high resolution image 230. In the example illustrated in FIG. 5B, the coordinates are calculated as (2, B), (3, B), (2, C), and (3, C).

Next, the brightness of the high resolution image 230 is calculated. In the example illustrated in FIG. 5B, the coordinate (2, B) of the high resolution image 230 is placed in the same coordinate as those of the pixel 221A of the inspection image 220A and the pixel 221B of the inspection image 220B. The brightness estimation unit 27 uses the intensities of the pixel 221A and the pixel 221B to estimate the brightness of the coordinate (2, B) of the high resolution image 230. For example, the brightness of the coordinate (2, B) of the high resolution image 230 is estimated as an average brightness between the pixel 221A and the pixel 221B. According to the above procedure, the high resolution image creation device 15 sequentially estimates the brightness of the image in units of sub-pixels, namely, a higher resolution than the resolution of a pixel to generate the high resolution image 230 of the inspection target 1.

In the example illustrated in FIG. 5, the two camera images 220A and 220B are used to describe the method of generating the high resolution image 230, but the high resolution image creation device 15 uses a plurality of camera images to generate a high resolution image. In the aforementioned example, the high resolution image 230 is generated by estimating the brightness of each coordinate of the high resolution image 230 as an average brightness between the two camera images 220A and 220B. Therefore, the contrast of the image is assumed to be low. In light of this point, the high resolution image creation device 15 performs contrast enhancement processing to enhance the contrast of the generated high resolution image 230.

Figure 6:
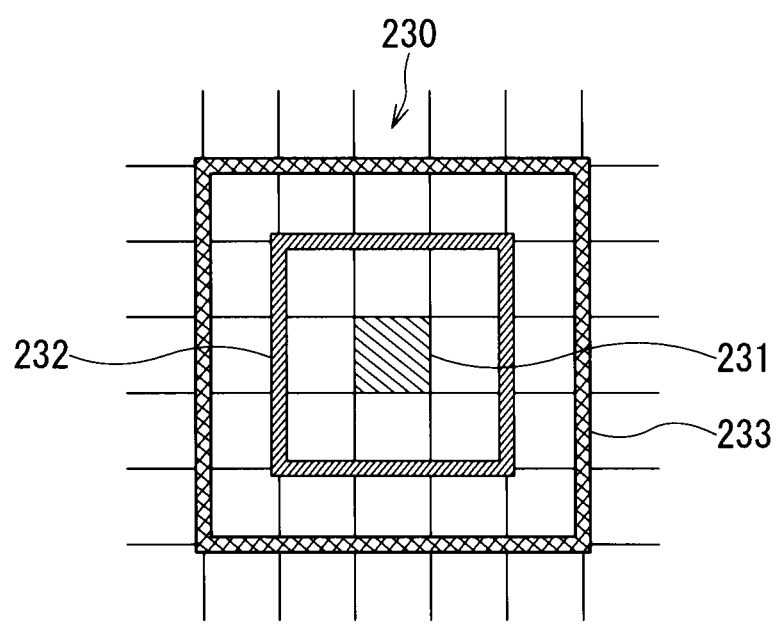
FIG. 6 is an explanatory drawing explaining the contrast enhancement method for the high resolution image generated by the high resolution image creation device illustrated in FIG. 1.

FIG. 6 is an explanatory drawing explaining the contrast enhancement method for the high resolution image 230 generated by the high resolution image creation device 15.

The contrast enhancement processing shown in FIG. 6 is described by taking an example of a process of enhancing the contrast of the pixel 231 of the high resolution image 230. First, assuming that the pixel 231 is located in the center of the image, a central range 232 and a peripheral range 233 are set. The peripheral range 233 must be wider than the central range 232. In the high resolution image 230 illustrated in FIG. 6, as an example, the central range 232 is 3×3 pixels, and the peripheral range 233 is 5×5 pixels.

The high resolution image creation device 15 calculates the average brightness of each of the central range 232 and the peripheral range 233, and calculates the brightness $(\alpha-\beta)$ by deducting the average brightness $\beta$ of the peripheral range 233 from the average brightness $\alpha$ of the central range 232. If the calculated brightness $(\alpha-\beta)$ is positive, the central range 232 is brighter than the peripheral range 233. On the contrary, if the brightness $(\alpha-\beta)$ is negative, the central range 232 is darker than the peripheral range 233. According to the present contrast enhancement processing, the brightness $(\alpha-\beta)$ calculated by the high resolution image creation device 15 is added to the brightness of the pixel 231. Then, if the central range 232 is brighter than the peripheral range 233, the pixel 231 is made much brighter; and if the central range 232 is darker than the peripheral range 233, the pixel 231 is made much darker, thereby enhancing the contrast of the pixel 231.

According to the first embodiment of the present invention, the inspector can confirm and inspect a high resolution image having a higher resolution than the resolution of the camera 11, thereby improving the defect visibility and increasing the inspection quality. Further, a high resolution image can be generated from an image when the camera 11 has a small movement or the lighting has a small change. Thus, the quality of the high resolution image is increased and the defect visibility is improved, thereby increasing the inspection quality.

Note that the present embodiment uses a configuration of inputting images taken by the camera 11 to the image input device 13, but another configuration of inputting video images recorded in an existing video tape or the like to the image input device 13 may be used. Further, the aforementioned image processing can be applied to not only monochrome images but also color images.

Second Embodiment

Figure 7:
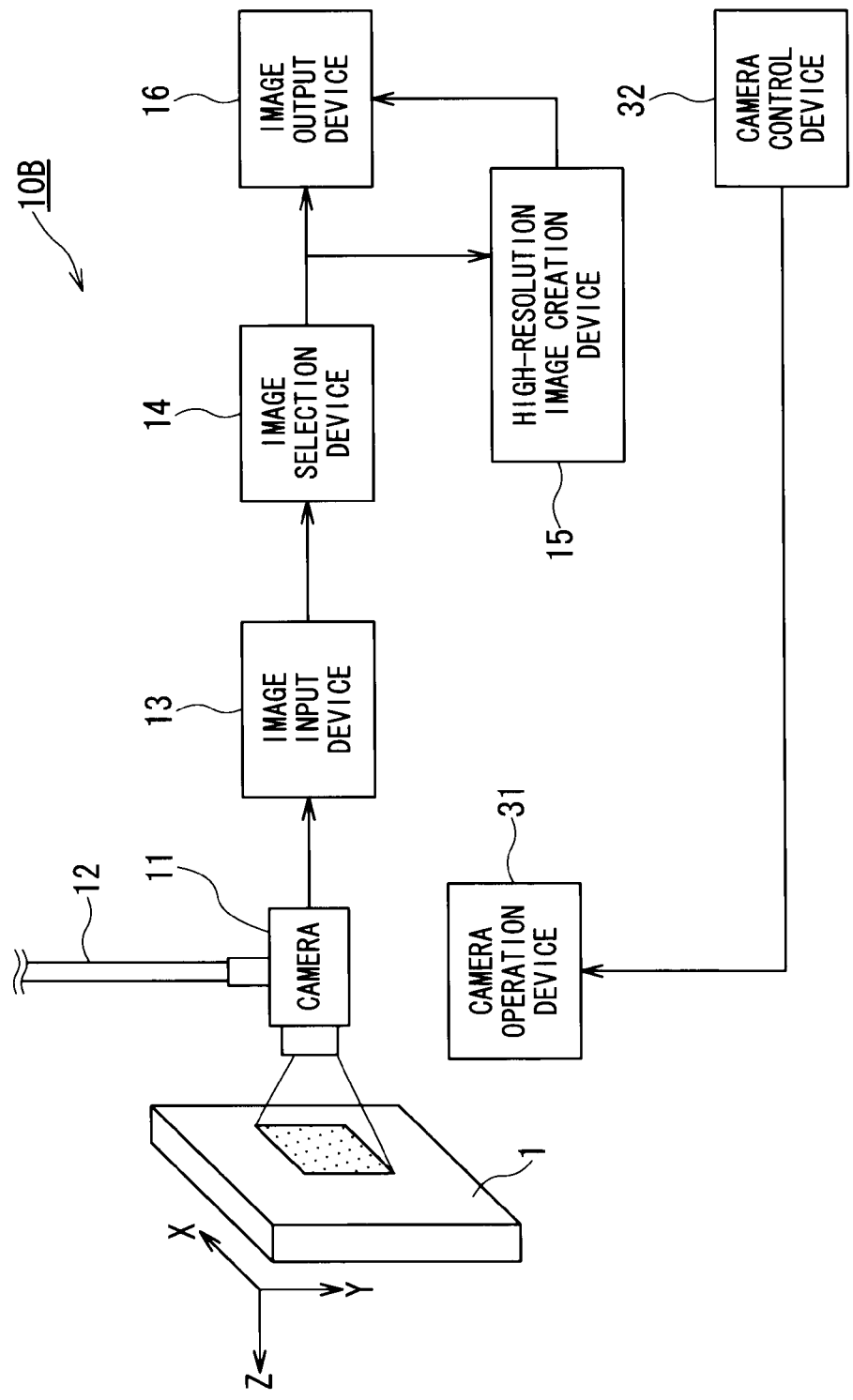
FIG. 7 is a block diagram illustrating a configuration of a visual inspection apparatus according to a second embodiment of the present invention.

FIG. 7 is a block diagram illustrating a configuration of a visual inspection apparatus (which will be referred to as "second visual inspection apparatus", hereinafter) 10B according to a second embodiment of the present invention. Note that the same reference numerals or characters in FIG. 7 are assigned to the same or similar components as those in FIG. 1, and the description thereof is omitted.

The second visual inspection apparatus 10B illustrated in FIG. 7 differs from the first visual inspection apparatus 10A illustrated in FIG. 1 in that the second visual inspection apparatus 10B further includes a camera operation device 31 for remotely operating the camera 11 and a camera control device 32 for remotely controlling the camera 11 and camera operation device 31. The second visual inspection apparatus 10B is not substantially different from the first visual inspection apparatus 10A in the other points. In light of this point, the present embodiment will be described by focusing on the camera operation device 31 and the camera control device 32.

Based on a control signal from the camera control device 32, the camera operation device 31 of the second visual inspection apparatus 10B remotely operates the camera 11 and/or the supporting device 12 to take images (obtain images) of the inspection target 1. In other words, the camera operation device 31 remotely performs a series of operations until images are taken including the movement of the camera 11.

The camera operation device 31 adjusts the FOV of the camera 11 and the imaging direction of the camera 11 so that the camera 11 can take an appropriate image of the inspection target 1. For example, the camera operation device 31 can move the camera 11 in the axis directions illustrated in FIG. 1 (the X-axis direction, the Y-axis direction and the Z-axis direction) and can adjust the imaging angle (the azimuth angle and the elevation angle) thereof and can adjust the focal length thereof.

The camera control device 32 receives an operator's operation input and sends a control signal according to the inputted operator's operation to the camera operation device 31 to control the operation of the camera operation device 31. The camera control device 32 controls the camera operation device 31 so as to prevent an abrupt change in angle of view of the camera 11 and an operation motion of the camera operation device 31 such as a movement of the camera 11 from occurring. Thereby, the image of the inspection target 1 taken without impairing the image feature quantity required for selection by the image selection device 14 is outputted from the camera 11.

In addition to the advantages obtained by the first embodiment, according to the second embodiment of the present invention, the operator can remotely operate the FOV and the imaging direction of the camera 11 as well as the camera control device 32 can control the camera operation device 31 so that the image selected by the image selection device 14 can be inputted from the camera 11 to the image selection device 14 at any time or any timing as needed. Therefore, a high resolution image can be generated at any time.

Third Embodiment

Figure 8:
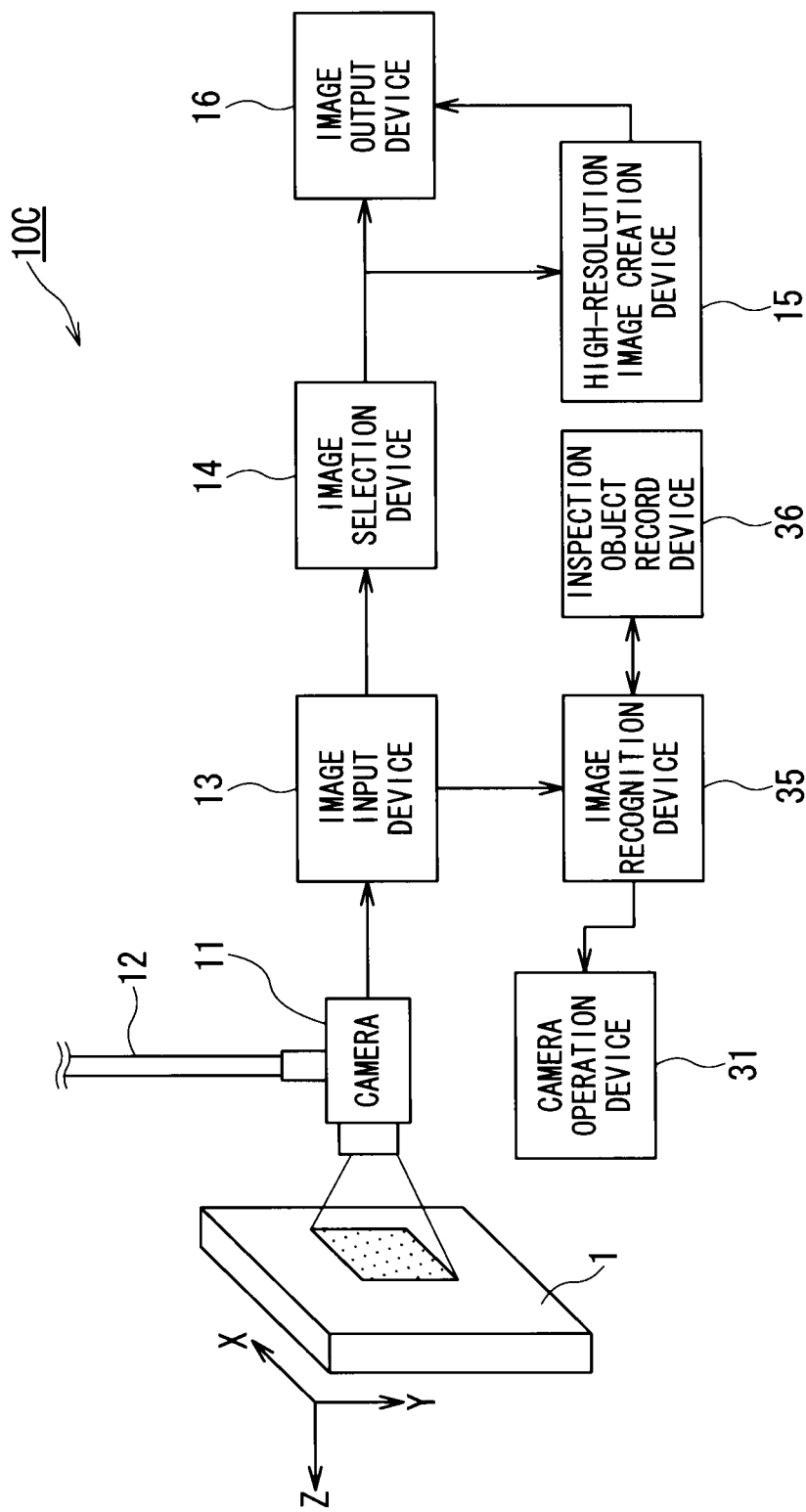
FIG. 8 is a block diagram illustrating a configuration of a visual inspection apparatus according to a third embodiment of the present invention.

FIG. 8 is a block diagram illustrating a configuration of a visual inspection apparatus (which will be referred to as "third visual inspection apparatus", hereinafter) 10C according to a third embodiment of the present invention. Note that the same reference numerals or characters in FIG. 8 are assigned to the same or similar components as those in FIGS. 1 and 7, and the description thereof is omitted.

The third visual inspection apparatus 10C illustrated in FIG. 8 differs from the first visual inspection apparatus 10A illustrated in FIG. 1 in that the third visual inspection apparatus 10C further includes a camera operation device 31; an image recognition device 35 for recognizing the inspection target 1; and an inspection object record device 36 for recording shape information of the inspection target 1. The third visual inspection apparatus 10C is not substantially different from the first visual inspection apparatus 10A in the other points. In light of this point, the present embodiment will be described by focusing on the image recognition device 35 and the inspection object record device 36.

The image recognition device 35 reads an image including shape information of the inspection target 1 recorded in the inspection object record device 36 as well as receives an image outputted from the image input device 13. Then, the image recognition device 35 compares and collates the image read from the inspection object record device 36 and the image outputted from the image input device 13 by image processing to recognize the inspection target 1.

The inspection object record device 36 stores an image having shape information of the inspection target 1. The stored image is read in response to a read request of the image recognition device 35.

Now, the operation of the third visual inspection apparatus 10C will be described.

Figure 9:
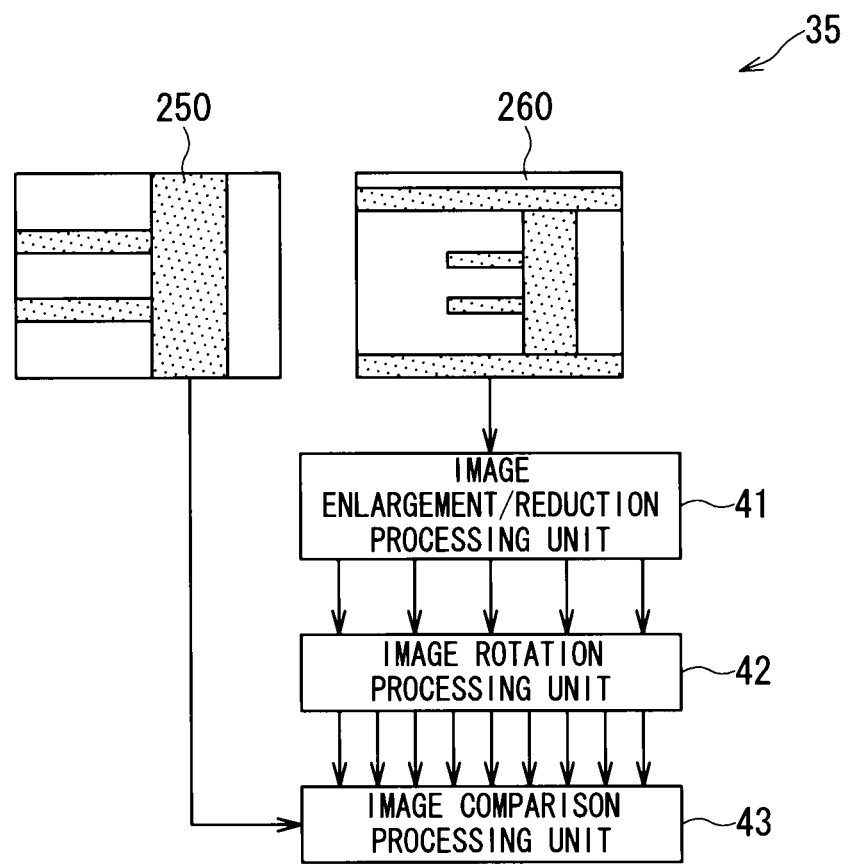
FIG. 9 is an explanatory drawing illustrating a configuration of the image recognition device of the visual inspection apparatus according to a third embodiment of the present invention and an image processing content performed by the image recognition device.

FIG. 9 is an explanatory drawing illustrating a configuration of the image recognition device 35 and an image processing content. Here, an image 250 is an image having shape information (inspection target shape information) of the inspection target 1, such as the image stored in the inspection object record device 36. Further, the image 260 illustrated in FIG. 9 is the image outputted from the image input device 13.

As illustrated in FIG. 9, the image recognition device 35 includes an image enlargement/reduction processing unit 41 for enlarging and reducing the image 260; an image rotation processing unit 42 for rotating an image outputted from the image enlargement/reduction processing unit 41; and an image comparison processing unit 43 for comparing and collating the image outputted from the image rotation processing unit 42 and the inspection target shape information (the image 250) read from the inspection object record device 36.

In the image recognition device 35, first, the image enlargement/reduction processing unit 41 performs image processing (image enlarging/reducing process) of enlarging or reducing the image 260 under a plurality of expansion or reduction conditions (magnification percentage). Then, the image rotation processing unit 42 performs image processing (image rotation process) of rotating each of the images enlarged or reduced under a different expansion or reduction condition, under a plurality of rotation conditions (rotation angle). Then, the image comparison processing unit 43 compares and collates a plurality of converted images outputted from the image rotation processing unit 42 and the image 250 as inspection target shape information read from the inspection object record device 36 to recognize the inspection target 1 from the image 260.

The image recognition device 35 recognizes the inspection target 1 from the image outputted from the image input device 13. Then, on the basis of recognized results, the image recognition device 35 controls the angle of view of the camera 11 and the operation direction of the camera operation device 31 so that the field of view of the camera 11 follows the inspection target 1. Consequently, the camera 11 can stably take an image of the inspection target 1.

According to the third embodiment of the present invention, in addition to the advantages obtained by the first embodiment, the inspection target 1 can be automatically recognized from the images acquired by the camera 11 and the FOV and the imaging direction of the camera 11 can be automatically controlled. As a result, an image to be selected by the image selection device 14 can be inputted at any time from the camera 11 to the image selection device 14 and thus a high resolution image can be generated at any time.

Fourth Embodiment

Figure 10:
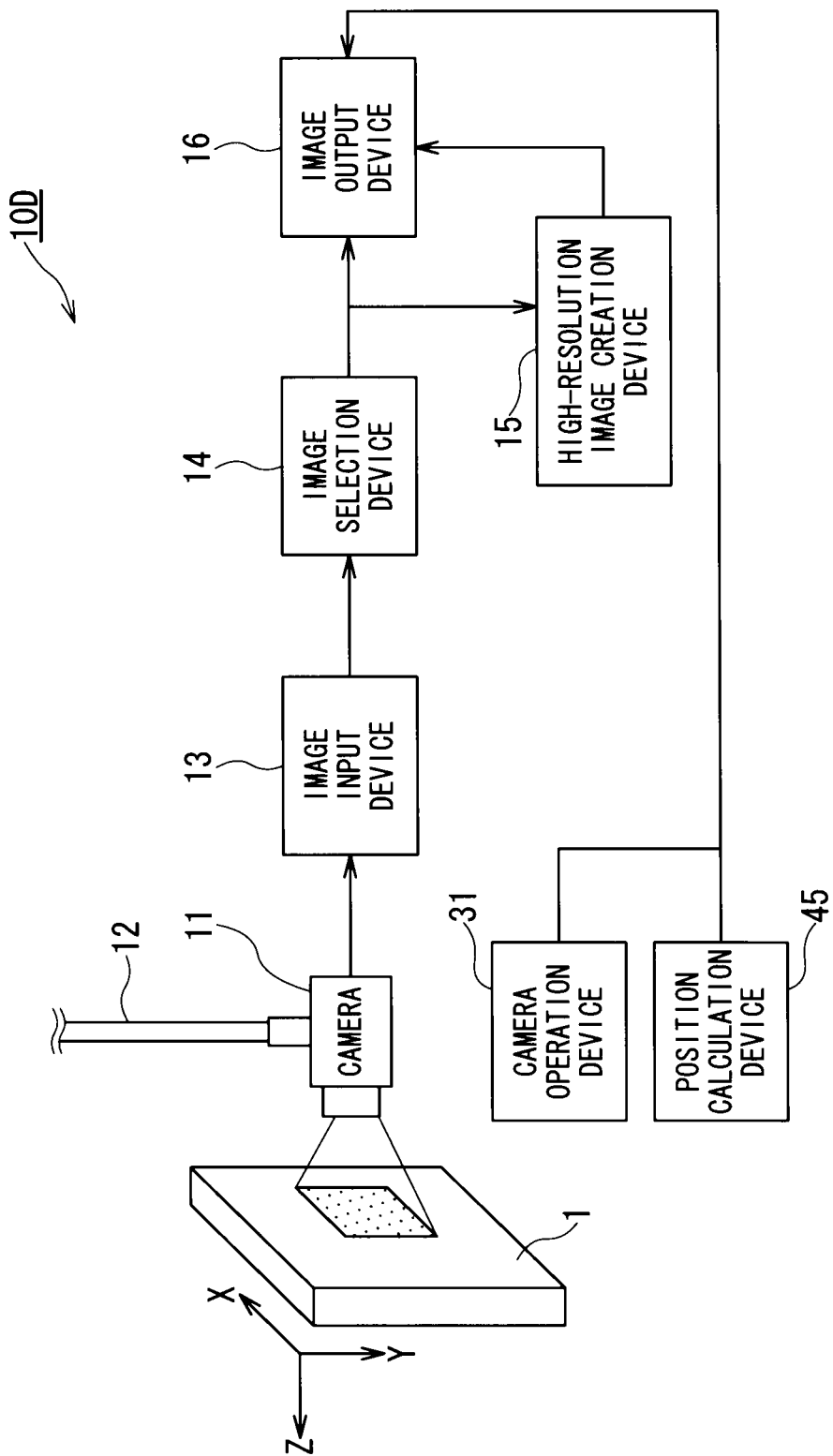
FIG. 10 is a block diagram illustrating a configuration of a visual inspection apparatus according to a fourth embodiment of the present invention.

FIG. 10 is a block diagram illustrating a configuration of a visual inspection apparatus (which will be referred to as "fourth visual inspection apparatus", hereinafter) 10D according to a fourth embodiment of the present invention. Note that the same reference numerals or characters in FIG. 10 are assigned to the same or similar components as those in FIGS. 1, 7 and 8, and the description thereof is omitted.

The fourth visual inspection apparatus 10D illustrated in FIG. 10 differs from the first visual inspection apparatus 10A illustrated in FIG. 1 in that the fourth visual inspection apparatus 10D further includes a camera operation device 31; and a position calculation (measurement) device 45 for measuring the position of the camera 11. The fourth visual inspection apparatus 10D is not substantially different from the first visual inspection apparatus 10A in the other points. In light of this point, the present embodiment will be described by focusing on the position calculation (measurement) device 45.

The position calculation device 45 of the fourth visual inspection apparatus 10D measures the position of the camera 11 using a GPS (Global Positioning System) and other methods and outputs the measured results to the image output device 16.

Now, the operation of the fourth visual inspection apparatus 10D will be described.

The fourth visual inspection apparatus 10D operates in the same manner as the first visual inspection apparatus 10A in such a manner that images of the inspection target 1 taken by the camera 11 are fed into the image input device 13; an image is selected by the image selection device 14; a high resolution image is generated by the high resolution image creation device 15; and further, the position calculation device 45 measures the position of the camera 11. The measured results of the position of the camera 11 are sent to the image output device 16 together with information of the operation position of the camera 11 sent from the camera operation device 31 and information of the angle of view of the camera 11.

Based on the position of the camera 11 measured by the position calculation device 45, the operation position of the camera 11, and the angle of view of the camera 11, the image output device 16 calculates the position of the inspection target 1 whose image is being taken by the camera 11, and displays the history of the positions of the inspection target 1 whose high resolution images are generated by the high resolution image creation device 15.

It should be noted that according to the present embodiment, based on the position of the camera 11 measured by the position calculation device 45, the operation position of the camera 11, and the angle of view of the camera 11, the image output device 16 calculates the position of the inspection target 1 whose image is being taken by the camera 11, but the position calculation device 45 may perform this calculation.

According to the fourth embodiment of the present invention, in addition to the advantages obtained by the first embodiment, the positions of the inspection target 1 whose high resolution images are generated can be understood, and thus the position information of the inspection target 1 can be added and the results can be recorded for management as well as the locations of a failure to inspect can be clarified, thereby preventing a failure to inspect.

Fifth Embodiment

Figure 11:
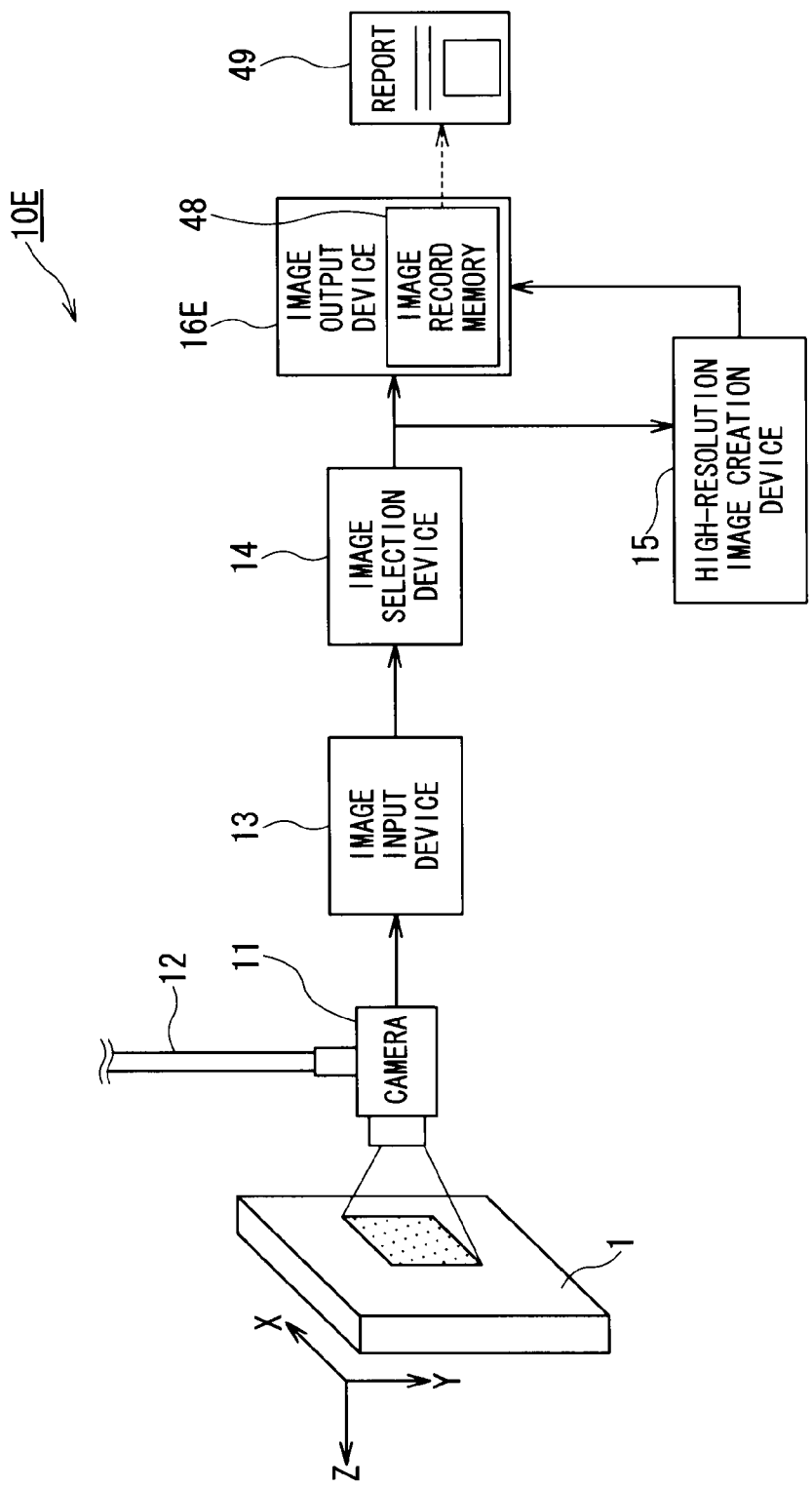
FIG. 11 is a block diagram illustrating a configuration of a visual inspection apparatus according to a fifth embodiment of the present invention.

FIG. 11 is a block diagram illustrating a configuration of a visual inspection apparatus (which will be referred to as "fifth visual inspection apparatus", hereinafter) 10E according to a fifth embodiment of the present invention. Note that the same reference numerals or characters in FIG. 11 are assigned to the same or similar components as those in FIGS. 1, 7, 8 and 10, and the description thereof is omitted.

The fifth visual inspection apparatus 10E illustrated in FIG. 11 differs from the first visual inspection apparatus 10A illustrated in FIG. 1 in that the fifth visual inspection apparatus 10E further includes an image output device 16E instead of the image output device 16. The fifth visual inspection apparatus 10E is not substantially different from the first visual inspection apparatus 10A in the other points. In light of this point, the present embodiment will be described by focusing on the image output device 16E.

The image output device 16E illustrated in FIG. 11 adds a image record memory 48 to the image output device 16 illustrated in FIG. 1 so as to record high resolution images displayed on the image output device 16. The fifth visual inspection apparatus 10E includes the image output device 16E having the image record memory 48. Therefore, if a defect is detected in the inspection target 1, a high resolution image having a higher resolution than the resolution of the image having an imaged defect can be stored.

Now, the operation of the fifth visual inspection apparatus 10E will be described.

In a conventional visual inspection, images of the camera 11 are recorded on a video tape or the like. If a defect is found in the inspection target, an inspector goes back to the office with the video tape, where the inspector creates the inspection record by checking the video images reproduced from the video tape.

In contrast to this, according to the fifth visual inspection apparatus 10E, while the inspector is checking the images displayed on the image output device 16 and when the inspector determines that there is a defect in the inspection target 1, the fifth visual inspection apparatus 10E can record the high resolution image displayed on the image output device 16 in the image record memory 48 of the image output device 16 in response to an operation input instruction by the inspector. Therefore, the inspector can use the high resolution images recoded in the image record memory 48 of the image output device 16 to create an inspection report 49.

According to the fifth embodiment of the present invention, in addition to the advantages obtained by the first embodiment, while the inspector is checking the images displayed on the image output device 16 and when the inspector determines that there is a defect, the corresponding high resolution image can be sequentially recorded in the image record memory 48 to create the inspection report 49, thereby eliminating a need to create the inspection report 49 by checking the reproduced video images, and thus reducing the binding hours of the inspector.

Sixth Embodiment

Figure 12:
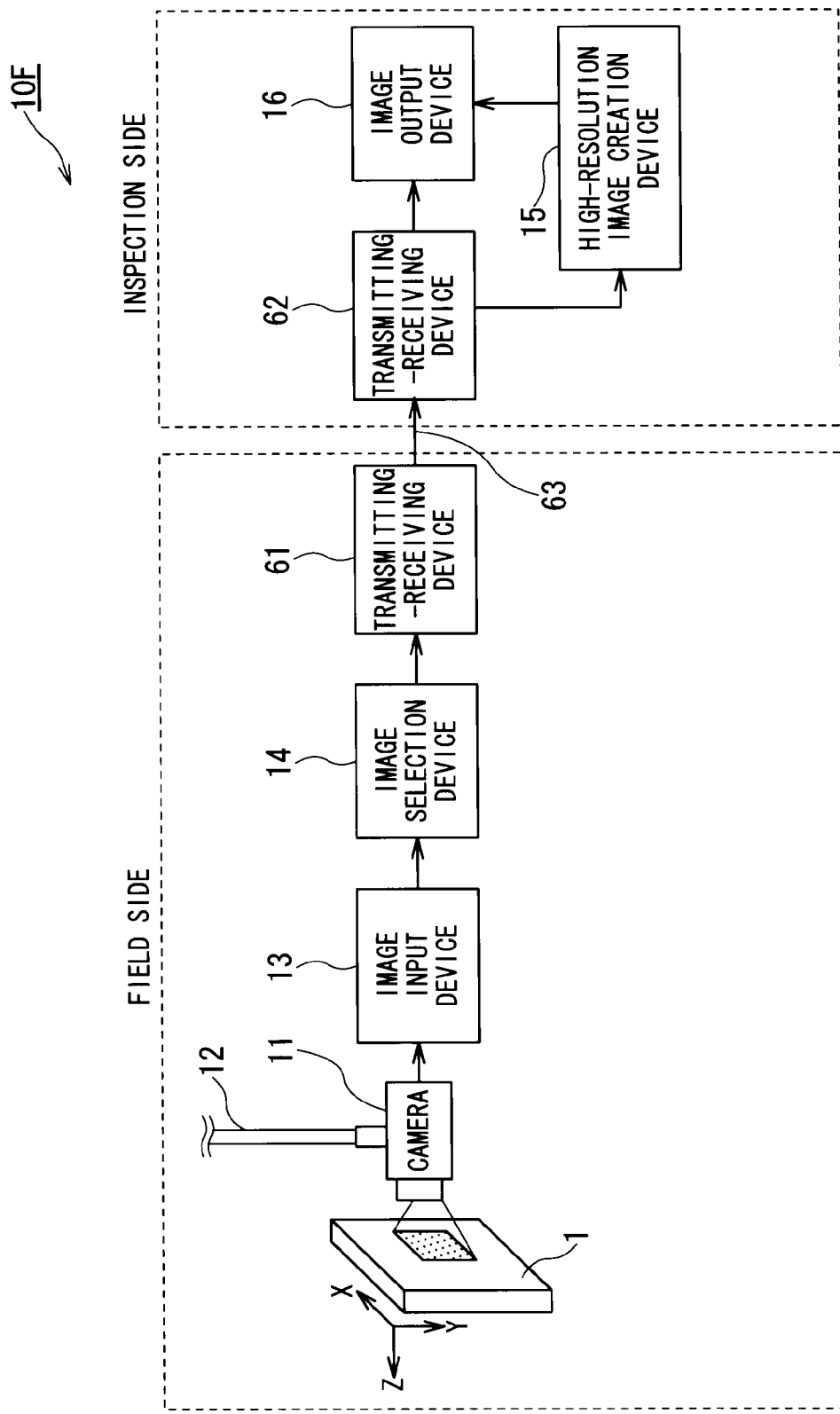
FIG. 12 is a block diagram illustrating a configuration of a visual inspection apparatus according to a sixth embodiment of the present invention.

FIG. 12 is a block diagram illustrating a configuration of a visual inspection apparatus (which will be referred to as "sixth visual inspection apparatus", hereinafter) 10F according to a sixth embodiment of the present invention. Note that the same reference numerals or characters in FIG. 12 are assigned to the same or similar components as those in FIGS. 1, 7, 8, 10 and 11, and the description thereof is omitted.

The sixth visual inspection apparatus 10F illustrated in FIG. 12 is configured by separating the first visual inspection apparatus 10A illustrated in FIG. 1 into two components: one on a field side; and another on an inspection (supervision) side. On the field side, the camera 11 takes an image of the inspection target 1. On the inspection side, an inspection is performed by actually controlling and supervising the field side from a location far from the field side. More specifically, the sixth visual inspection apparatus 10F illustrated in FIG. 12 differs from the first visual inspection apparatus 10A illustrated in FIG. 1 in that the sixth visual inspection apparatus 10F further includes a transmitting/receiving device 61 on the field side; and a transmitting/receiving device 62 on the inspection side; and the transmitting/receiving devices 61 and 62 are connected to each other via a communication line 63. The sixth visual inspection apparatus 10F is not substantially different from the first visual inspection apparatus 10A in the other points. In light of this point, the present embodiment will be described by focusing on the transmitting/receiving devices 61 and 62, and the communication line 63.

The transmitting/receiving devices 61 and 62 each have a function to transmit and receive image data. The transmitting/receiving device 61 on the field side receives the selected image from the image selection device 14 and transmits the received image to the transmitting/receiving device 62 on the inspection side via the communication line 63. Then, the transmitting/receiving device 62 on the inspection side receives the image transmitted from the transmitting/receiving device 61 on the field side via the communication line 63. Consequently, the transmitting/receiving device 62 on the inspection side receives the selected image from the image selection device 14 via the transmitting/receiving device 61 on the field side and the communication line 63.

Now, the operation of the sixth visual inspection apparatus 10F will be described.

The transmitting/receiving device 61 on the field side transmits the inspection image selected by the image selection device 14 to the transmitting/receiving device 62 on the inspection side using the communication line 63. The communication line 63 is implemented, for example, by a telephone line, a LAN, a wireless LAN, an infrared communication, a satellite communication, and the like.

The transmitting/receiving device 62 on the inspection side outputs the inspection image transmitted from the transmitting/receiving device 61 on the field side to the high resolution image creation device 15 and the image output device 16. The high resolution image creation device 15 generates a high resolution image from the inspection image outputted from the transmitting/receiving device 61 and outputs the high resolution image to the image output device 16. The image output device 16 displays the inspection image outputted from the transmitting/receiving device 62 and the high resolution image generated by the high resolution image creation device 15 to be provided to the inspector.

According to the sixth embodiment of the present invention, in addition to the advantages obtained by the first embodiment, a further remote, highly accurate visual inspection can be performed even in a location (inspection side) far from the field side using the communication line 63. Moreover, a high resolution image having a high resolution is generated from the inspection image transmitted and received via the communication line 63, thereby reducing the amount of data than by transmitting and receiving the high resolution image via the communication line 63. Therefore, even a remote inspection using the communication line 63 with a limited transmission band can provide a highly accurate inspection. Further, the inspector can check the imaging situations such as the position of the camera 11 and the position of the inspection target 1 from continuously transmitted inspection images. Therefore, the same inspection as the conventional inspection performed on the field can be performed using the inspection images transmitted and received via the communication line 63 without a need to be on the field.

Seventh Embodiment

Figure 13:
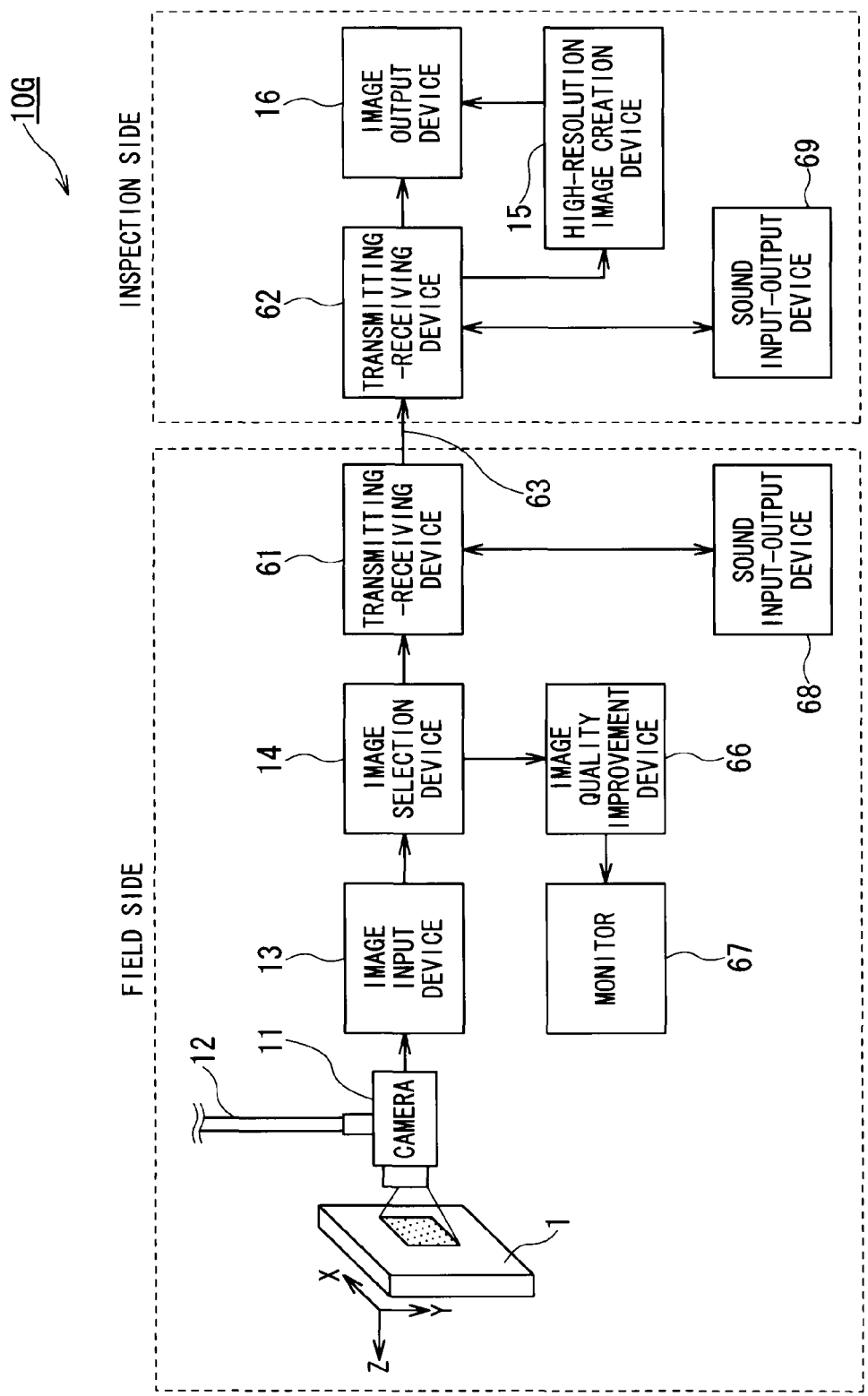
FIG. 13 is a block diagram illustrating a configuration of a visual inspection apparatus according to a seventh embodiment of the present invention.

FIG. 13 is a block diagram illustrating a configuration of a visual inspection seventh visual inspection apparatus (which will be referred to as "seventh visual inspection apparatus", hereinafter) 10G according to a seventh embodiment of the present invention. Note that the same reference numerals or characters in FIG. 13 are assigned to the same or similar components as those in FIGS. 1, 7, 8 and 10-12, and the description thereof is omitted.

The seventh visual inspection apparatus 10G illustrated in FIG. 13 differs from the sixth visual inspection apparatus 10F illustrated in FIG. 12 in that the seventh visual inspection apparatus 10G further includes an image quality improvement device 66 for improving the image quality of an inspection image selected by the image selection device 14 by image selection processing; a monitor 67 for displaying the image undergoing image improvement by the image quality improvement device 66; and sound input-output devices 68 and 69 for inputting and outputting voice (sound) of an operator on the field side and an inspector on the inspection side. The seventh visual inspection apparatus 10G is not substantially different from the sixth visual inspection apparatus 10F in the other points. In light of this point, the present embodiment will be described by focusing on the image quality improvement device 66, the monitor 67, the sound input-output devices 68 and 69.

The image quality improvement device 66 has a function to improve the image quality of an inspection image selected by the image selection device 14 by image processing. The image quality improvement device 66 inputs an image from the image selection device 14, improves the image quality of the inputted image, and outputs the image undergoing image quality improvement to the monitor 67.

The monitor 67 displays the image undergoing image quality improvement received from the image quality improvement device 66. The inspector can check the inspection image of the inspection target 1 by the image undergoing image quality improvement displayed on the monitor 67.

The sound input-output devices 68 and 69 each have a function to input and output voice (sound) of an operator on the field side and an inspector on the inspection side. The sound input-output devices 68 and 69 implement intercommunication between an operator on the field side and an inspector on the inspection side by voice. The sound input-output device 68 is provided on the field side and the sound input-output device 69 is provided on the inspection side.

Now, the operation of the seventh visual inspection apparatus 10G will be described.

According to a conventional visual inspection, an inspector visually checks the video images of the camera 11 displayed on the monitor 67. If a not determined but assumed to be defect appears, the inspector checks the video images again by moving the camera 11 closer to the inspection target 1.

According to the seventh visual inspection apparatus 10G, while the inspector is checking the images displayed on the image output device 16 and when the inspector determines that recheck is required to move the camera 11 closer to the inspection target 1, the inspector vocally instructs the operator.

According to the seventh visual inspection apparatus 10G, when the voice of the inspector is inputted to the sound input-output device 69 on the inspection side, the sound input-output device 69 transmits the voice of the inspector to the sound input-output device 68 on the field side via the transmitting/receiving device 62 on the inspection side and the communication line 63. The sound input-output device 68 on the field side outputs the voice of the inspector to communicate the instruction of the inspector to the operator.

Further, the voice such as an operation confirmation of the operator is inputted to the sound input-output device 68 on the field side to be transmitted to the sound input-output device 69 on the inspection side via the transmitting/receiving device 61 on the field side and the transmitting/receiving device 62 on the inspection side. Then, the sound input-output device 69 on the inspection side outputs the voice of the operator to communicate the voice of the operator to the inspector.

Through these operations, the operator on the field side and the inspector on the inspection side perform remote inspection through dialog. At the same time, the inspection image selected by the image selection device 14 is inputted to the image quality improvement device 66. The image quality improvement device 66 improves the image quality of the image by image processing to be displayed on the monitor 67. The image quality improvement device 66 performs the same image processing as the high resolution image creation device 15, such as increasing the resolution of the image and enhancing the contrast of the image so as to improve the image quality of the image to be outputted.

On the field side, the operator can confirm which position of the inspection target 1 the inspector wants to recheck through dialog with the sound input-output device 68 on the field side and the image displayed on the monitor 67. Thus, the operator can perform operations such as moving the camera 11 closer to the inspection target 1.

According to the seventh embodiment of the present invention, in addition to the advantages obtained by the sixth embodiment, the operator can confirm the position of the recheck operation such as moving the camera 11 closer to the inspection target 1 through dialog and by the images displayed on the monitor 67, thereby allowing the intention of the remote inspector to be accurately conveyed to the operator, and thus improving operability. Therefore, the same inspection as the conventional inspection performed on the field can be performed using the images transmitted and received via the communication line 63.

Eighth Embodiment

Figure 14:
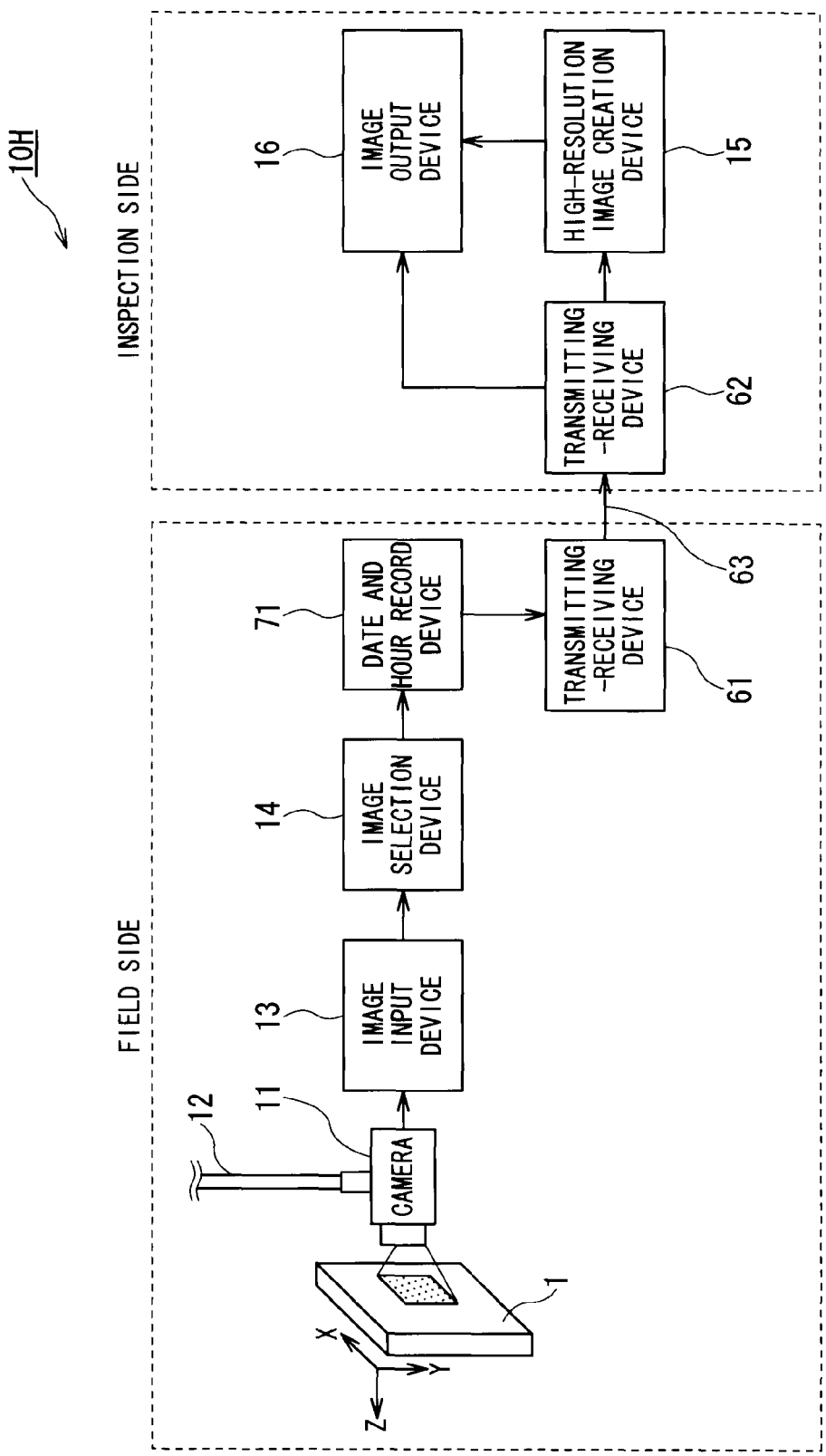
FIG. 14 is a block diagram illustrating a configuration of a visual inspection apparatus according to an eighth embodiment of the present invention.

FIG. 14 is a block diagram illustrating a configuration of a visual inspection apparatus (which will be referred to as "eighth visual inspection apparatus", hereinafter) 10H according to an eighth embodiment of the present invention. Note that the same reference numerals or characters in FIG. 14 are assigned to the same or similar components as those in FIGS. 1, 7, 8 and 10-13, and the description thereof is omitted.

The eighth visual inspection apparatus 10H illustrated in FIG. 14 differs from the sixth visual inspection apparatus 10F illustrated in FIG. 12 in that the eighth visual inspection apparatus 10H further includes a date and hour record device 71 for drawing the date and time on the inspection image selected by the image selection device 14. The eighth visual inspection apparatus 10H is not substantially different from the sixth visual inspection apparatus 10F in the other points. In light of this point, the present embodiment will be described by focusing on the date and hour record device 71.

The date and hour record device 71 has a function to add information of the current date and time to the inputted image. For example, the information is drawn on a predetermined position such as an upper left of the inputted image.

Now, the operation of the eighth visual inspection apparatus 10H will be described.

The inspection image selected by the image selection device 14 is inputted to the date and hour record device 71. Then, the date and hour record device 71 draws the current date and time on a position such as an upper left of the inputted inspection image. The inspection image having the current date and time drawn by the date and hour record device 71 is transmitted from the transmitting/receiving device 61 on the field side to the transmitting/receiving device 62 on the inspection side via the communication line 63 and is displayed on the image output device 16. At the same time, the current date and time information drawn on the inspection image is transmitted from the date and hour record device 71 to the image output device 16 via the transmitting/receiving device 62.

The image output device 16 reads the date and time drawn on the inspection image by image processing, and compares the read date and time with the date and time information received from the date and hour record device 71 to confirm that the received inspection image is the inspection image transmitted from the field side. Moreover, the inspector can compare the date and time of the inspection image being displayed on the image output device 16 and the current date and time to confirm that the inspection image being checked is the inspection image transmitted from the field side.

According to the eighth embodiment of the present invention, in addition to the advantages obtained by the sixth embodiment, when a remote inspection is performed using the communication line 63, the inspector can confirm that the inspection image being checked is the inspection image transmitted from the field side to the inspection side, thereby guaranteeing that the inspection is performed on the correct image. Consequently, even if an image transmission error occurs due to an unexpected failure of the communication line 63 or a system trouble, the error is quickly identified and thus an appropriate measure can be taken.

Ninth Embodiment

Figure 15:
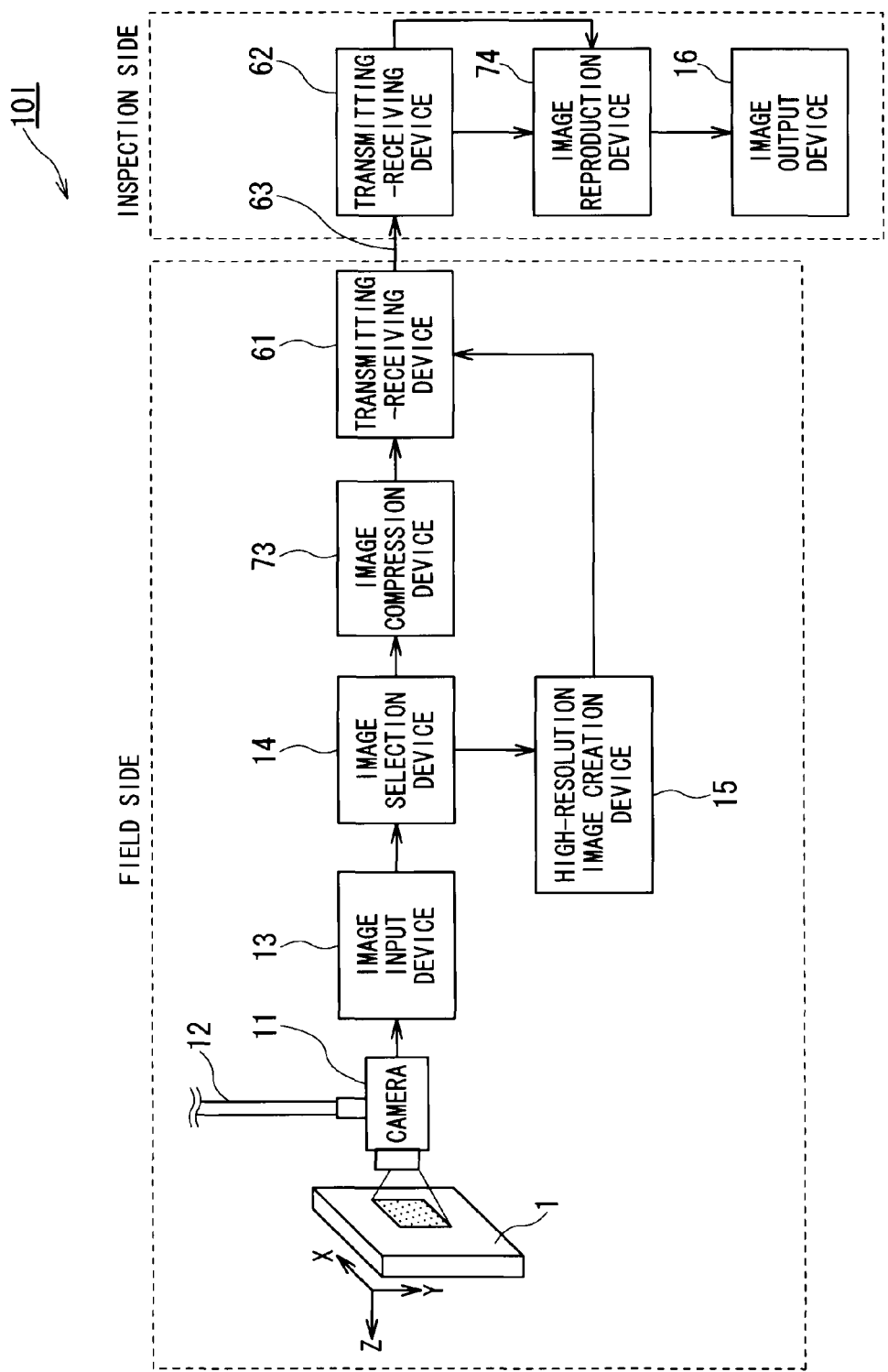
FIG. 15 is a block diagram illustrating a configuration of a visual inspection apparatus according to a ninth embodiment of the present invention.

FIG. 15 is a block diagram illustrating a configuration of a visual inspection apparatus (which will be referred to as "ninth visual inspection apparatus", hereinafter) 10I according to a ninth embodiment of the present invention. Note that the same reference numerals or characters in FIG. 15 are assigned to the same or similar components as those in FIGS. 1, 7, 8 and 10-14, and the description thereof is omitted.

The ninth visual inspection apparatus 10I illustrated in FIG. 15 differs from the sixth visual inspection apparatus 10F illustrated in FIG. 12 in that the ninth visual inspection apparatus 10I further includes an image compression device 73 for compressing an image provided on the field side and an image reproduction (decompression) device 74 for restoring (decompressing) an image provided on the inspection side. The ninth visual inspection apparatus 10I is not substantially different from the sixth visual inspection apparatus 10F in the other points. In light of this point, the present embodiment will be described by focusing on the image compression device 73 and the image reproduction device 74.

The image compression device 73 has an image compression function. The image compression device 73 video-compresses an image outputted from the image selection device 14 by applying an image compression system such as an MPEG and outputs the compressed image to the transmitting/receiving device 61.

The image reproduction device 74 has a function to restore (decompress) the image compressed by the image compression device 73. The image reproduction device 74 restores the compressed image received from the image compression device 73 via the transmitting/receiving device 61, the communication line 63, and the transmitting/receiving device 62.

Now, the operation of the ninth visual inspection apparatus 10I will be described.

The image selection device 14 outputs the selected image to the high resolution image creation device 15 and the image compression device 73. The high resolution image creation device 15 uses the image outputted from the image selection device 14 to generate a high resolution image and outputs the high resolution image to the transmitting/receiving device 61 provided on the field side.

The image compression device 73 video-compresses the image outputted from the image selection device 14 using a video image compression such as an MPEG and outputs the compressed image to the transmitting/receiving device 61 on the field side. The transmitting/receiving device 61 on the field side transmits the high resolution image outputted from the high resolution image creation device 15 and the video-compressed inspection image outputted from the image compression device 73 on the field side to the transmitting/receiving device 62 provided on the inspection side via the communication line 63.

The transmitting/receiving device 62 on the inspection side outputs the high resolution image received from the transmitting/receiving device 61 on the field side to the image output device 16 and outputs the compressed inspection image to the image reproduction device 74 on the inspection side. The image reproduction device 74 restores the compressed inspection image and outputs the restored inspection image to the image output device 16. The image output device 16 displays the restored inspection image and the high resolution image to be provided to the inspector.

According to the ninth embodiment of the present invention, in addition to the advantages obtained by the sixth embodiment, a remote, highly accurate visual inspection can be performed using the communication line 63 even in a location far from the field. The compressed inspection image and the high resolution image aggregating time-space image information are transmitted via the communication line 63, and thus the amount of data can be reduced than by transmitting the uncompressed inspection image. Therefore, even a remote inspection using a line with a limited transmission band can provide a highly accurate visual inspection.

Tenth Embodiment

Figure 16:
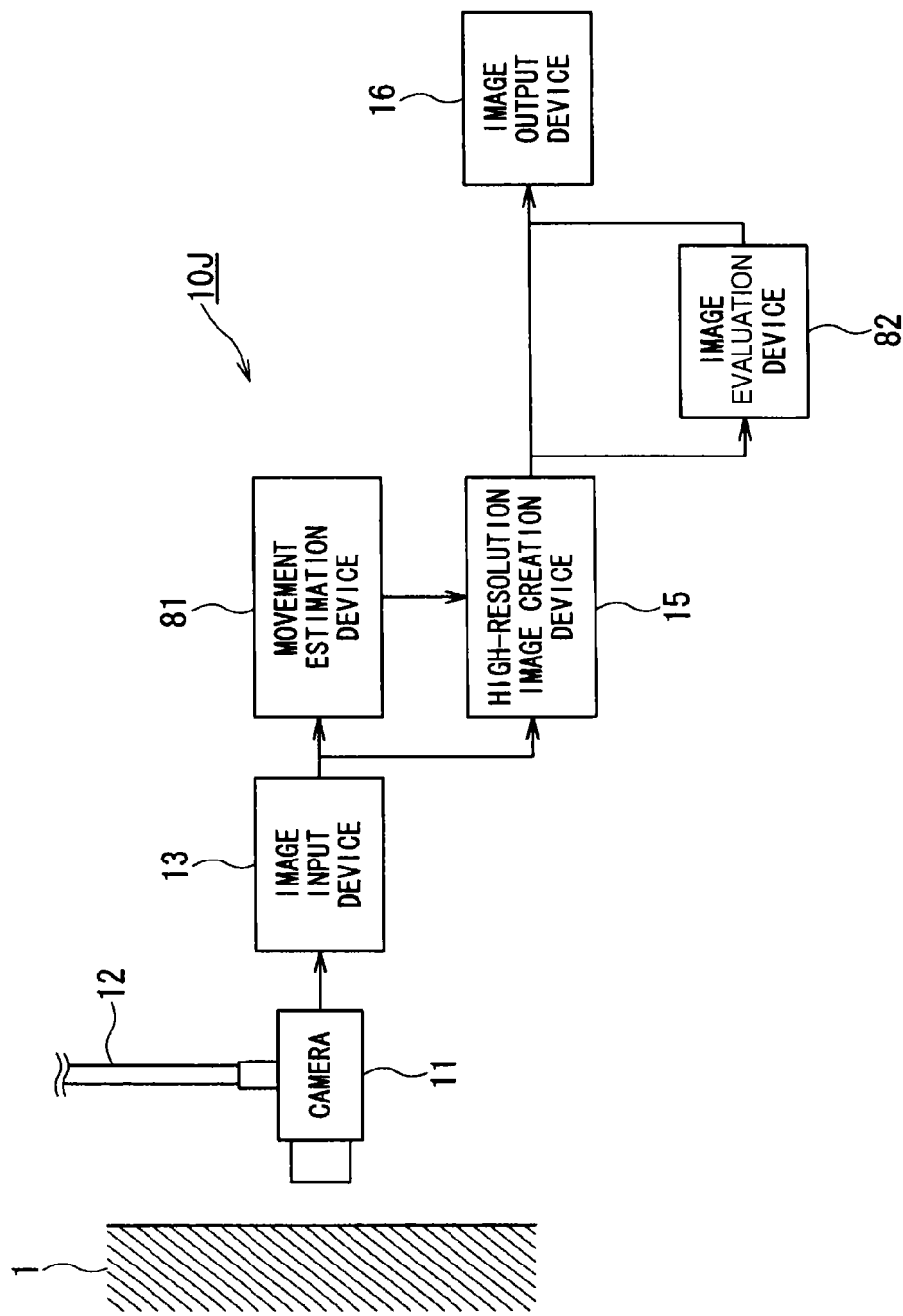
FIG. 16 is a block diagram illustrating a configuration of a visual inspection apparatus according to a tenth embodiment of the present invention.

FIG. 16 is a block diagram illustrating a configuration of a visual inspection apparatus (which will be referred to as "tenth visual inspection apparatus", hereinafter) 10J according to a tenth embodiment of the present invention. Note that the same reference numerals or characters in FIG. 16 are assigned to the same or similar components as those in FIGS. 1, 7, 8 and 10-15, and the description thereof is omitted.

The tenth visual inspection apparatus 10J illustrated in FIG. 16 differs from the first visual inspection apparatus 10A illustrated in FIG. 1 in that the tenth visual inspection apparatus 10J includes a movement estimation device 81 instead of the image selection device 14, and further includes an image evaluation device 82. The tenth visual inspection apparatus 10J is not substantially different from the first visual inspection apparatus 10A in the other points. In light of this point, the present embodiment will be described by focusing on the movement estimation device 81 and the image evaluation device 82.

The tenth visual inspection apparatus 10J includes an image input device 13, a movement estimation device 81 for estimating the movement of the camera 11 or the inspection target 1 (movement of the camera 11 according to the present embodiment); a high resolution image creation device 15; an image evaluation device 82 for evaluating the quality of a high resolution image generated by the high resolution image creation device 15; and an image output device 16 for presenting an inspector with the high resolution image generated by the high resolution image creation device 15 and the quality of the high resolution image evaluated by the image evaluation device 82.

The movement estimation device 81 of the tenth visual inspection apparatus 10J sequentially records an camera image (digital image) outputted from the image input device 13; compares the recorded image with a new image outputted from the image input device 13 by image processing; and estimates the scanning motion (movement) of the camera 11 in the two images at sub-pixel accuracy, namely, an accuracy of higher resolution than the resolution of a pixel. As an example of the estimation method, expansion processing is performed on the aforementioned two images to increase the resolution of the images, and the two enlarged images are compared with each other by block matching based on brightness dispersion to estimate the movement position of the camera 11. By referring to FIG. 17, the block matching performed by the movement estimation device 81 will be described.

Figures 17A, 17B:
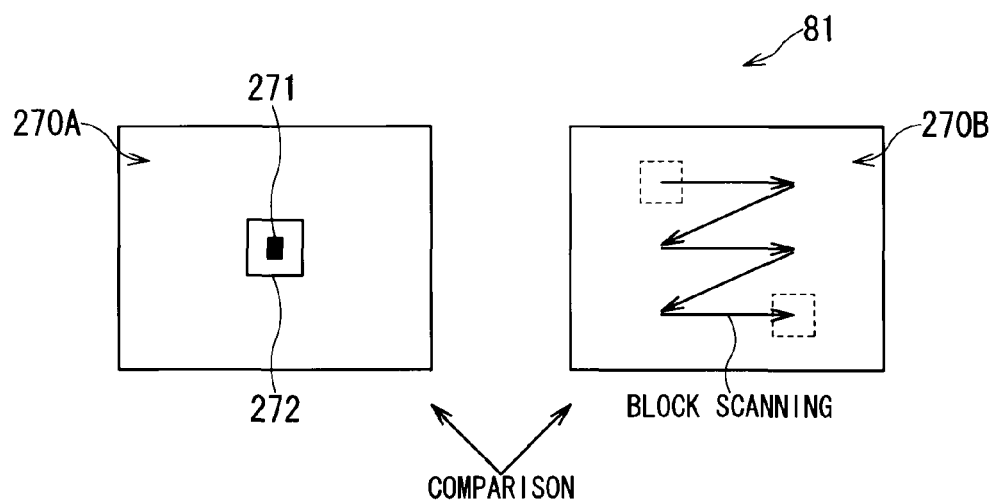
FIG. 17A is a schematic view illustrating an image enlarging an already stored camera image.
FIG. 17B is a schematic view illustrating an image enlarging a new camera image.

FIG. 17 each are an explanatory drawing explaining the block matching performed by the movement estimation device 81. FIG. 17A is a schematic view illustrating an enlarged image 270A enlarging an already stored camera image. FIG. 17B is a schematic view illustrating an enlarged image 270B enlarging a new camera image.

The block matching uses the enlarged image 270A obtained by performing expansion processing on a camera image previously held by the movement estimation device 81 and the enlarged image 270B obtained by performing expansion processing on a new image outputted from the image input device 13 to estimate the movement of the camera 11 of the enlarged image 270A with each pixel of the enlarged image 270A in the enlarged image 270B.

More specifically, a rectangular block 272 is set around a pixel 271A so as to estimate the position of a movement of the camera 11 of the enlarged image 270A, and the brightness dispersion inside the rectangular block 272 is calculated. If the brightness dispersion inside the rectangular block 272 is equal to or greater than a certain threshold, block scanning (indicated by the arrow illustrated in FIG. 17B) is performed on the enlarged image 270B to obtain the position where the brightness dispersion is the most similar to that of the rectangular block 272 in the enlarged image 270B by a method of using the difference in brightness or the correlation of brightness. The position which is determined by this processing such that the brightness dispersion is the most similar to that of the rectangular block 272 is the movement estimated position of the camera 11 in the enlarged image 270B of the pixel 271. The block matching performs the above processing on every pixel of the enlarged image 270A.

Conversely, the block matching is not performed on a pixel where the brightness dispersion inside the rectangular block 272 is less than the certain threshold, and thus the position of a movement of the camera 11 in the enlarged image 270B cannot be estimated. Regarding the pixel on which the block matching is not performed, the position of a movement of the camera 11 in the enlarged image 270B is estimated from the results of peripheral pixels on which the block matching is performed.

Figure 18:
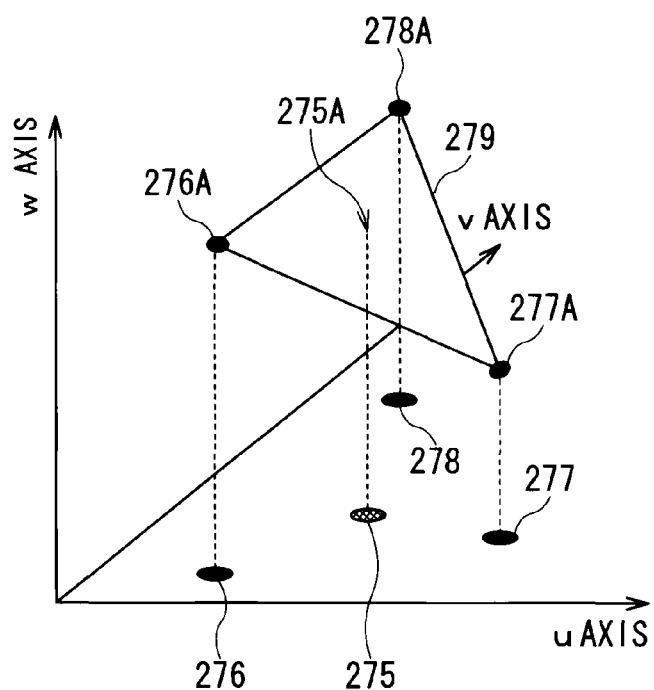
FIG. 18 is an explanatory drawing explaining the movement estimation device, of the visual inspection apparatus according to a tenth embodiment of the present invention, for estimating the movement of the camera.

As an example of the method, as illustrated in FIG. 19, a search is performed on at least three pixels 276, 277, and 278 which surround the pixel 275 estimating the movement position of the camera 11 and on which the block matching has been performed. Then, the searched three pixels 276, 277, and 278 are used to generate a three-dimensional space, assuming that the lateral direction of the image is a U axis, the vertical direction of the image is a V axis, and the direction of an estimated position with respect to the U axis and the V axis estimating the movement position of the three pixels 276, 277, and 278 is a W axis. In this three-dimensional space, calculation is made to obtain a virtual plane 279 connecting estimated positions 276A, 277A, and 278A, whose movements have been estimated, each corresponding to the three pixels 276, 277, and 278 respectively. Then, assuming that an estimated position 275A of the pixel 275 estimating the movement position of the camera 11 is located on the virtual plane 279, calculation is made to obtain an estimated position 275A (value on the W axis) of the pixel 275 estimating the movement position of the camera 11 from the estimated positions on the U axis and the V axis of the pixel 275. Note that, in example illustrated in FIG. 18, the virtual plane 279 is assumed using the three pixels 276, 277, and 278, but may be any calculable polynomial plane using three or more pixels.

As described above, the block matching is performed only on the rectangular block 272 having high brightness dispersion. High brightness dispersion means that the image has a characteristic texture and suits for matching. Conversely, low brightness dispersion means that the image does not have a characteristic texture but has a uniform texture and thus matching may not produce reliable results. In this manner, a determination is made based on the brightness dispersion as to whether the block matching is to be performed on each rectangular block 272, and thus the movement position of the camera 11 can be reliably estimated. Note that the movement position of the camera 11 may be estimated and determined using information other than the brightness dispersion as long as the texture characteristics of the image can be evaluated.

Note that the present embodiment will be described by focusing on the method of estimating the movement of the camera 11 from a video image of the camera 11, but the movement position of the camera 11 may be geometrically estimated using drive information of the drive apparatus and physical information between the inspection target 1 and the camera 11.

The image evaluation device 82 illustrated in FIG. 16 evaluates the quality of a high resolution image generated by the high resolution image creation device 15 by checking whether or not the increase in resolution exceeding the pixel resolution of the camera 11 is correctly made, whether or not the degree of the object visibility is appropriately improved due to the increase in resolution, and the like. The image evaluation method applied to the image evaluation device 82 will be described by referring to FIGS. 19 and 20.

(First Image Evaluation Method)

Figures 19A, 19B:
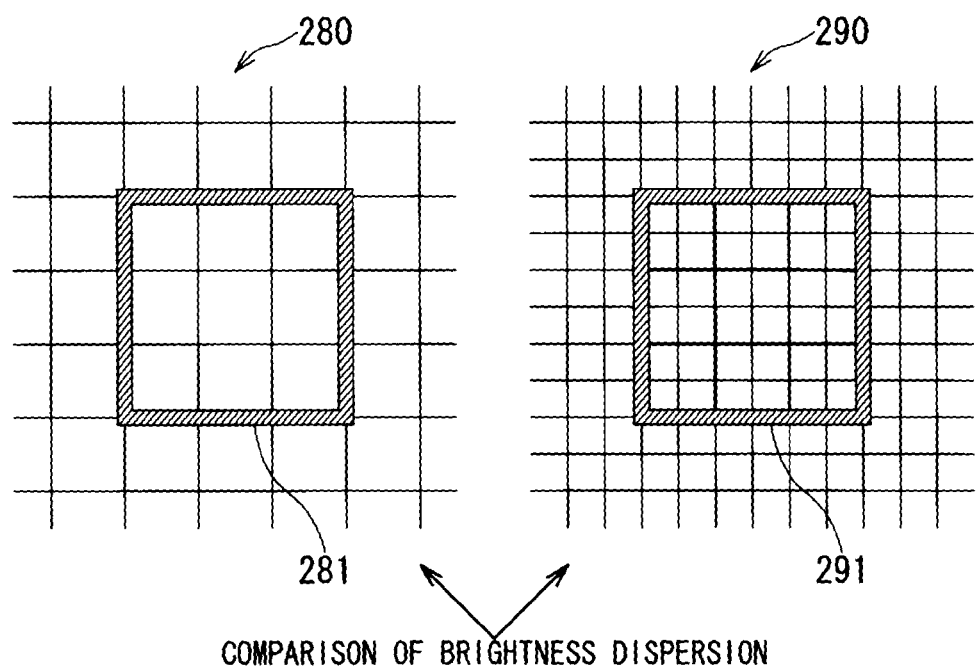
FIG. 19A is a schematic view illustrating a camera image.
FIG. 19B is a schematic view illustrating a high resolution image.

FIG. 19 each are an explanatory drawing explaining a first image evaluation method applied to the image evaluation device 82. FIG. 19A is a schematic view illustrating a camera image 280. FIG. 19B is a schematic view illustrating a high resolution image 290. Note that in FIG. 19, as an example, the resolution of the high resolution image 290 doubles the resolution of camera image 280.

The image evaluation device 82 sets local ranges 281 and 291 to a camera image 280 outputted from the image input device 13 and the high resolution image 290 generated by the high resolution image creation device 15 respectively. The local range 291 of the high resolution image 290 is set to a position and a range where the resolution of the pixels of the local range 281 of the camera image 280 is increased using the movement estimated position of the camera 11 estimated by the movement estimation device 81 which is used when the high resolution image creation device 15 generates the high resolution image 290.

Then, the brightness dispersion of each of the local range 281 of the camera image 280 and the local range 291 of the high resolution image 290 is calculated. Then, the ratio F of the calculated brightness dispersion between the local ranges 281 and 291 of the camera image 280 and the high resolution image 290 respectively is calculated by the following expression (1).

[Expression 1]

$$F = A/B \qquad (1),$$

, where F denotes a brightness dispersion ratio, A denotes a brightness dispersion of the local range 291 of the high resolution image 290, and B denotes a brightness dispersion of the local range 281 of the camera image 280. In general, an increase in resolution of an image improves visibility such that the outline and the design of the object are more clearly seen, and thus improves the brightness dispersion. In other words, if the brightness dispersion A of the high resolution image 290 is greater than the brightness dispersion B of the camera image 280, the object visibility of the high resolution image 290 is assumed to be higher than that of the camera image 280. Consequently, the image evaluation device 82 evaluates such that if the ratio F exceeds 1, the quality of the image is improved; and if the ratio F is equal to or less than 1, the quality of the image is not improved.

The image evaluation device 82 performs the processing on all of the plurality of pixels of the camera image 280 used when the high resolution image creation device 15 generates the high resolution image 290 and outputs the evaluation results such as the average value of the ratios F, the percentage of the ratios F exceeding 1 with respect to the number of evaluations, and the like to the image output device 16.

(Second Image Evaluation Method)

Figure 20A:
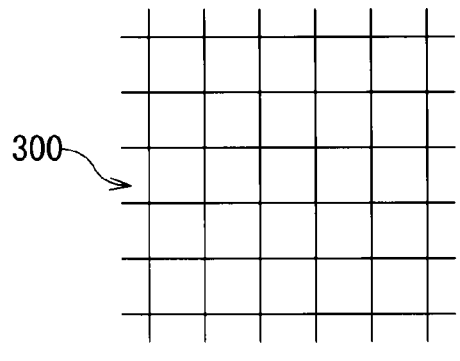
FIG. 20A is a schematic view illustrating a camera image.
Figure 20B:
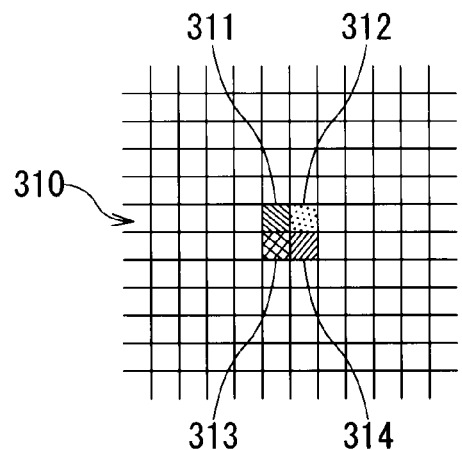
FIG. 20B is a schematic view illustrating a high resolution image.
Figure 20C:
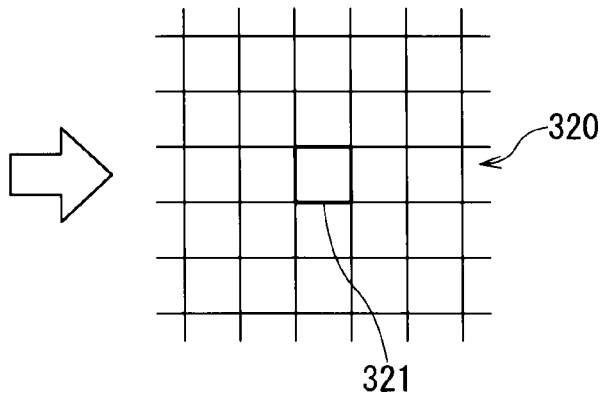
FIG. 20C is a schematic view illustrating a simulated camera image.

FIG. 20 each are an explanatory drawing explaining a second image evaluation method of evaluating a high resolution image performed by the image evaluation device 82. FIG. 20A is a schematic view illustrating a camera image 300. FIG. 20B is a schematic view illustrating a high resolution image 310. FIG. 20C is a schematic view illustrating a simulated camera image 320. Note that in the examples illustrated in FIG. 20, the pixel resolution of the high resolution image 310 is set to double that of the camera image 300.

The image evaluation device 82 generates a simulated camera image 320 as a converted image by inversely converting the high resolution image 310 generated by the high resolution image creation device 15 to an image having the same pixel resolution as that of the camera image 300. In the explanatory drawings of FIG. 20, the pixel resolution of the high resolution image 310 is set to double that of the camera image 300, and thus the horizontal 2 pixels×vertical 2 pixels of the high resolution image 310 correspond to one pixel of the camera image 300.

For example, the image evaluation device 82 calculates an average brightness of the four pixels: a pixel 311, a pixel 312, a pixel 313, and a pixel 314 of the high resolution image 310 and outputs the average brightness as the brightness of the pixel 321 of the simulated camera image 320. In the processing, the image evaluation device 82 generates the simulated camera image 320 by sequentially shifting pixels as not to overlap a combination of the four pixels 311 to 314 of the high resolution image 310 (in the present example, the resolution of high resolution image 310 is double and thus two pixels are shifted).

Then, the image evaluation device 82 evaluates the image quality of the high resolution image 310 by comparing the camera image 300 and the simulated camera image 320. When the camera image 300 and the simulated camera image 320 are compared, alignment is performed so that the camera image 300 and the simulated camera image 320 are moved to the same position from the movement estimated position of the camera 11 estimated by the movement estimation device 81 which is used when the high resolution image creation device 15 generates the high resolution image 310, and then obtains a difference image by calculating the difference between the images 300 and 320.

If the high resolution image 310 is correctly generated, the brightness difference between the camera image 300 and the simulated camera image 320 is close to zero. For this reason, the image evaluation device 82 sets any threshold to the difference image. If the average brightness of the difference image is equal to or less than the threshold, the image evaluation device 82 evaluates that the high resolution image 310 is correctly generated; and if the average brightness of the difference image exceeds the threshold, the image evaluation device 82 evaluates that the high resolution image 310 is not correctly generated due to an effect of an external lighting or the like.

The image evaluation device 82 performs the processing on all of the images, i.e., simulated camera image 320 and the plurality of camera images 300 used when the high resolution image creation device 15 generates the high resolution image 310 and outputs the evaluation results such as the average value of the difference images to the image output device 16.

Note that the evaluation of the quality of a high resolution image by the image evaluation device 82 may be performed each time the inspection target 1 is inspected, or may be performed before and after the inspection target 1 is inspected without being performed during the inspection so as to increase the efficiency of the inspection.

According to the tenth embodiment of the present invention, the following effects (1) and (2) are obtained.

(1) The image input device 13 generates digital images (camera images) by performing digital processing on the time-series video images of the inspection target 1 taken by the camera 11 obtained by a movement of the camera 11 or the inspection target 1; and the high resolution image creation device 15 uses the images to generate high resolution images each having a higher pixel resolution than the pixel resolution of the camera 11 by software and presents the inspector with the high resolution images via the image output device 16. As a result, the inspector visually checks the inspection target 1 based on the high resolution images and thus the reliability of inspection by the inspector can be improved as well as the inspection time can be reduced than by using video images by a camera having a narrow FOV to inspect a wide inspection range.

(2) The image evaluation device 82 quantitatively evaluates the quality of the high resolution images generated by the high resolution image creation device 15 using the first or second evaluation method to present the inspector with the high resolution images via the image output device 16. Therefore, the reliability of inspection using the high resolution images can be guaranteed.

Eleventh Embodiment

Figure 21:
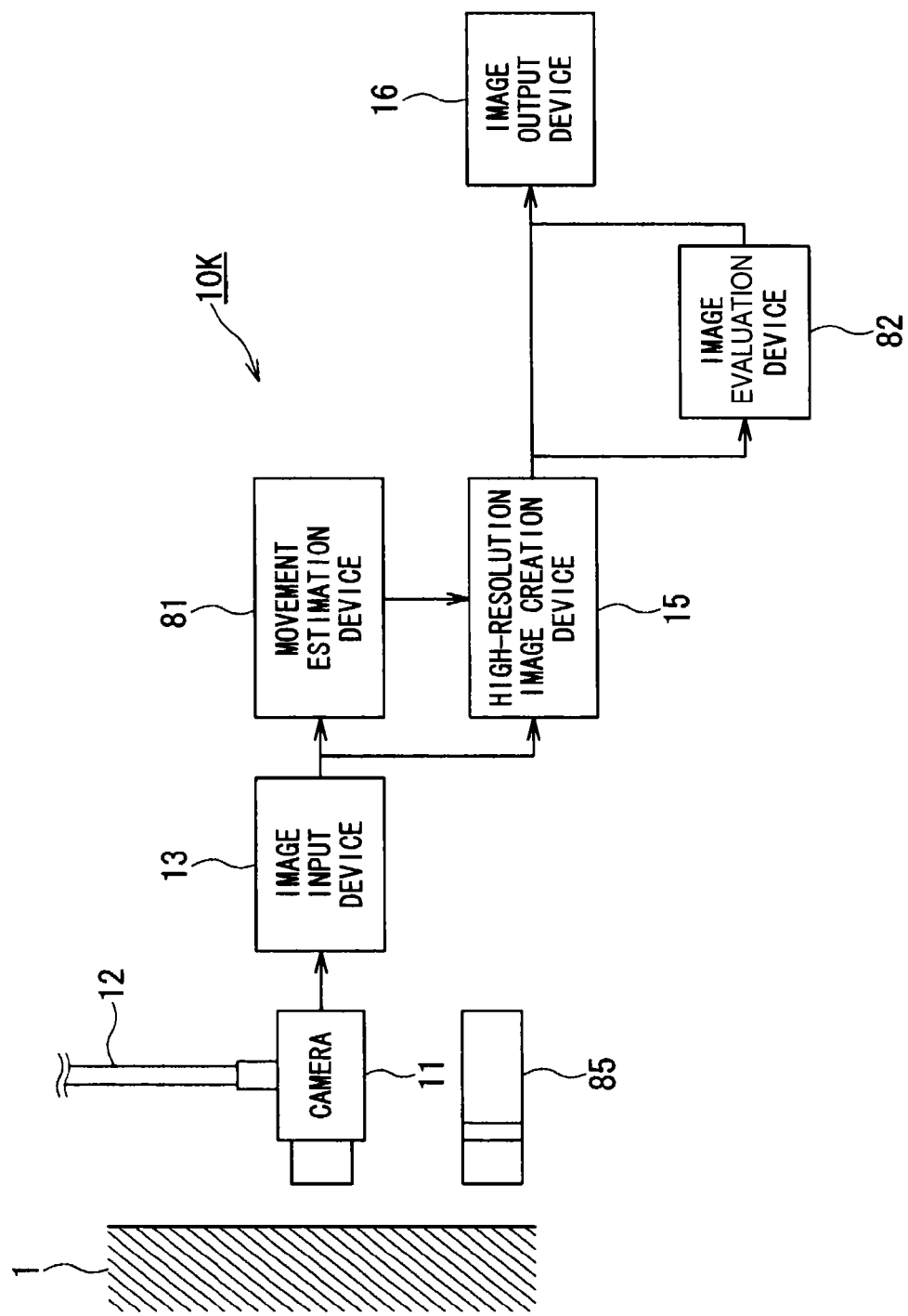
FIG. 21 is a block diagram illustrating a configuration of a visual inspection apparatus according to an eleventh embodiment of the present invention.

FIG. 21 is a block diagram illustrating a configuration of a visual inspection apparatus (which will be referred to as "eleventh visual inspection apparatus", hereinafter) 10K according to an eleventh embodiment of the present invention. Note that the same reference numerals or characters in FIG. 21 are assigned to the same or similar components as those in FIGS. 1, 7, 8 and 10-16, and the description thereof is omitted.

The eleventh visual inspection apparatus 10K illustrated in FIG. 21 differs from the tenth visual inspection apparatus 10J illustrated in FIG. 16 in that the eleventh visual inspection apparatus 10K further includes a light projection device (light projector) 85 which moves independently of the camera 11 and projects a known light pattern to the inspection target 1 so as to use the light pattern projected by the light projection device 85 to evaluate the quality of a high resolution image. The eleventh visual inspection apparatus 10K is not substantially different from the tenth visual inspection apparatus 10J in the other points. In light of this point, the present embodiment will be described by focusing on the light projection device 85.

The eleventh visual inspection apparatus 10K illustrated in FIG. 21 adds the light projection device 85 to the tenth visual inspection apparatus 10J (the image input device 13, the movement estimation device 81, the high resolution image creation device 15, the image evaluation device 82 and the image output device 16).

The light projection device 85 of the eleventh visual inspection apparatus 10K, for example, projects a line-shaped light pattern with a known width onto the inspection target 1. Then, the camera 11 takes an image of the inspection target 1 in such a manner that a line-shaped light pattern 331 projected from the light projection device 85 onto the inspection target 1 can fit into one image together with the inspection target 1.

Figure 22:
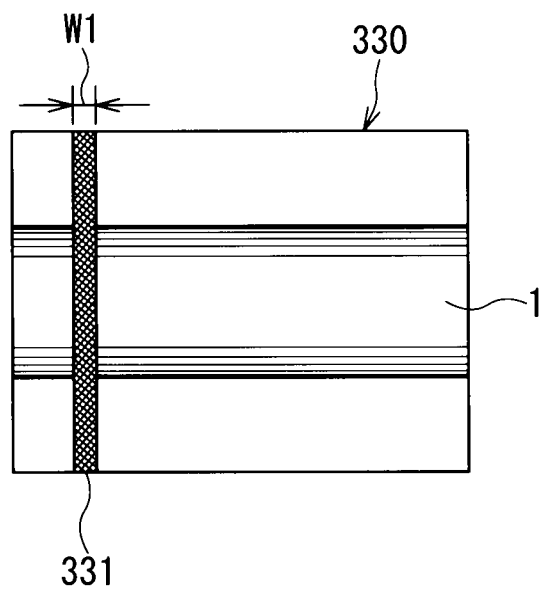
FIG. 22 is an explanatory drawing explaining the evaluation method, of evaluating a high resolution image, performed by the image evaluation device of the visual inspection apparatus according to an eleventh embodiment of the present invention.

FIG. 22 is an explanatory drawing explaining the evaluation method of evaluating a high resolution image 330 performed by the image evaluation device 82 of the eleventh visual inspection apparatus 10K. By referring to FIG. 22, the evaluation method of evaluating the high resolution image 330 performed by the image evaluation device 82 of the eleventh visual inspection apparatus 10K will be described.

According to the eleventh visual inspection apparatus 10K, for example, the light projection device 85 projects the line-shaped light pattern 331 with a known width onto the inspection target 1. Then, as illustrated in FIG. 22, the camera 11 takes an image of the inspection target 1 in such a manner that the line-shaped light pattern 331 projected by the light projection device 85 onto the inspection target 1 can fit into one image together with the inspection target 1.

The image evaluation device 82 extracts the line-shaped light pattern 331 projected onto the inspection target 1 from the high resolution image 330 generated by the high resolution image creation device 15 by image processing and measures the size of a place with a known size in the light pattern 331, for example, a line width W1. Then, the image evaluation device 82 compares the known size (e.g., line width W1) in the light pattern 331 and a size (e.g., line width W1) measured from the high resolution image 330 by image processing to calculate measurement accuracy.

In general, when the resolution of an image is increased, the outline and the design of the object can be observed in detail, and thus the measurement accuracy improves. Consequently, based on the high or low of the calculated measurement accuracy, the image evaluation device 82 performs quality evaluation of the high resolution image 330 such as by checking the degree of improvement of the visibility of the high resolution image 330 and whether or not the high resolution image 330 is correctly generated. Then, the image evaluation device 82 outputs the evaluation results to the image output device 16.

Note that according to the present embodiment, the image evaluation device 82 compares between the known size of the light pattern 331 and the size obtained by measurement from the high resolution image 330; but the same image processing may be performed on an image generated by the image input device 13 to measure the size of the light pattern; and the measurement accuracy by the image may be compared with the measurement accuracy by the high resolution image 330; if the measurement accuracy of the high resolution image 330 is higher than the measurement accuracy of the image, the image evaluation device 82 may evaluate that the visibility is increased and the high resolution image 330 is correctly generated.

According to the eleventh embodiment of the present invention, in addition to the advantages (1) and (2) obtained by the tenth embodiment, the following effect (3) is obtained.

(3) The image evaluation device 82 compares between the known size of the light pattern 331 which the light projection device 85 projects onto the inspection target 1 and the size of the light pattern 331 extracted from the high resolution image 330 generated by the high resolution image creation device 15 to obtain the measurement accuracy. Then, based on the measurement accuracy, the image evaluation device 82 evaluates the quality of the high resolution image 330. Therefore, in this case, the high resolution image 330 can be accurately evaluated, and thus the reliability of inspection using the high resolution image 330 can be surely guaranteed.

Twelfth Embodiment

Figure 23:
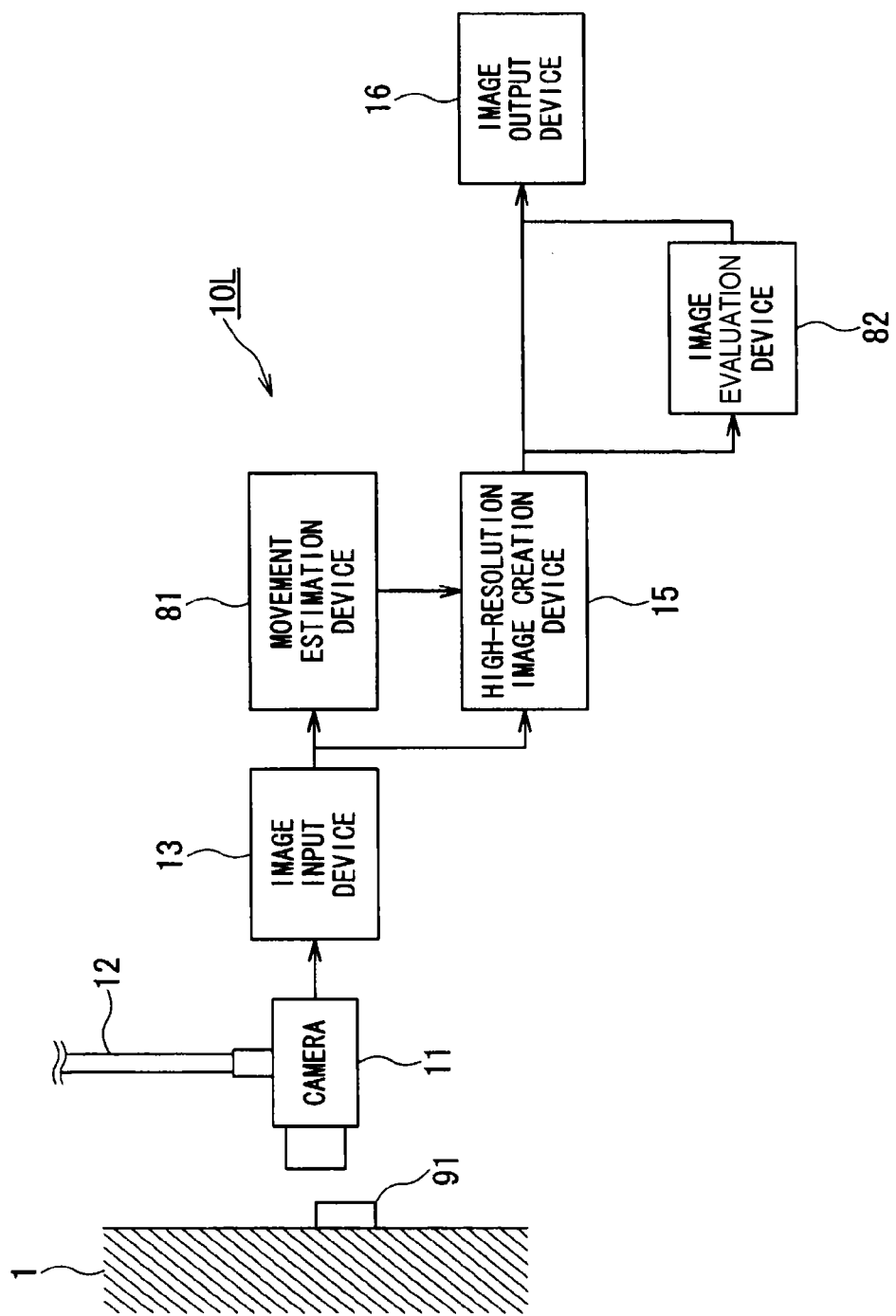
FIG. 23 is a block diagram illustrating a configuration of a visual inspection apparatus according to a twelfth embodiment of the present invention.

FIG. 23 is a block diagram illustrating a configuration of a visual inspection apparatus (which will be referred to as "twelfth visual inspection apparatus", hereinafter) 10L according to a twelfth embodiment of the present invention. Note that the same reference numerals or characters in FIG. 23 are assigned to the same or similar components as those in FIGS. 1, 7, 8, 10-16 and 21, and the description thereof is omitted.

The twelfth visual inspection apparatus 10L illustrated in FIG. 23 differs from the tenth visual inspection apparatus 10J illustrated in FIG. 16 in that the twelfth visual inspection apparatus 10L further includes a test piece 91 of a known size provided near the inspection target 1; and a video image of the test piece 91 is used to evaluate the quality of a high resolution image. The twelfth visual inspection apparatus 10L is not substantially different from the tenth visual inspection apparatus 10J in the other points. In light of this point, the present embodiment will be described by focusing on the test piece 91.

The test piece 91 has, for example, a line-shaped wire 92 of a known width and is provided near the inspection target 1. According to the twelfth visual inspection apparatus 10L, the camera 11 takes an image of the inspection target 1 so that the inspection target 1 and the test piece 91 are fit into one image.

Figure 24:
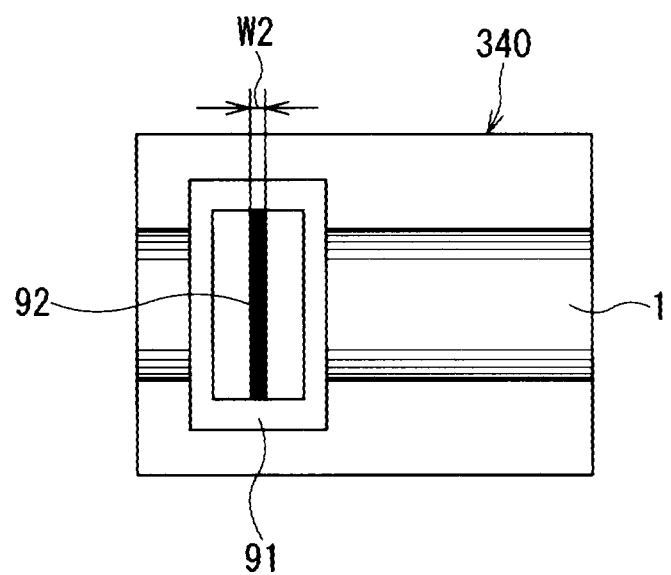
FIG. 24 is an explanatory drawing explaining the evaluation method, of evaluating a high resolution image, performed by the image evaluation device of the visual inspection apparatus according to a twelfth embodiment of the present invention.

FIG. 24 is an explanatory drawing explaining the evaluation method of evaluating a high resolution image 340 performed by the image evaluation device 82 of the twelfth visual inspection apparatus 10L. By referring to FIG. 24, the evaluation method of evaluating the high resolution image 340 performed by the image evaluation device 82 of the twelfth visual inspection apparatus 10L will be described.

According to the twelfth visual inspection apparatus 10L, the camera 11 takes an image of the inspection target 1 so that the test piece 91 provided near the inspection target 1 and having the line-shaped wire 92 of a known width and the inspection target 1 are fit into one image.

The image evaluation device 82 extracts the test piece 91 from the high resolution image 340 generated by the high resolution image creation device 15 by image processing, and measures the size of the location of a known size in the line-shaped wire 92, for example, a width W2 of the line-shaped wire 92. Next, the image evaluation device 82 uses the line-shaped wire 92 to compare between the known size (e.g., line width W2) and the size (e.g., line width W2) obtained by measurement from the high resolution image 340 by image processing to calculate the measurement accuracy.

In general, when the resolution of an image is increased, the outline and the design of the object can be observed in detail, and thus the measurement accuracy improves. Consequently, based on the high or low of the calculated measurement accuracy, the image evaluation device 82 performs quality evaluation of the high resolution image 340 such as by checking the degree of improvement of the visibility of the high resolution image 340 and whether or not the high resolution image 340 is correctly generated. Then, the image evaluation device 82 outputs the evaluation results to the image output device 16.

Note that in the example illustrated in FIG. 24, the description focused on one line-shaped wire 92 as the test piece 91, but a plurality of line-shaped wires 92 each having a different width may be used; and based on the correlation between the wire width (size) of each line-shaped wire 92 and the measurement accuracy, the image evaluation device 82 may evaluate the quality of the high resolution image 340 in detail such as by calculating a minimum width visible by the high resolution image 340.

According to the twelfth embodiment of the present invention, in addition to the advantages (1) and (2) obtained by the tenth embodiment, the following effect (4) is obtained.

(4) The image evaluation device 82 compares between the known size (width X) of the line-shaped wire 92 of the test piece 91 and the size (width W2) of the line-shaped wire 92 extracted from the high resolution image 340 generated by the high resolution image creation device 15 to obtain the measurement accuracy. Then, based on the measurement accuracy, the image evaluation device 82 evaluates the quality of the high resolution image 340. Therefore, in this case, the high resolution image 340 can be accurately evaluated, and thus the reliability of inspection using the high resolution image 340 can be surely guaranteed.

Thirteenth Embodiment

Figure 25:
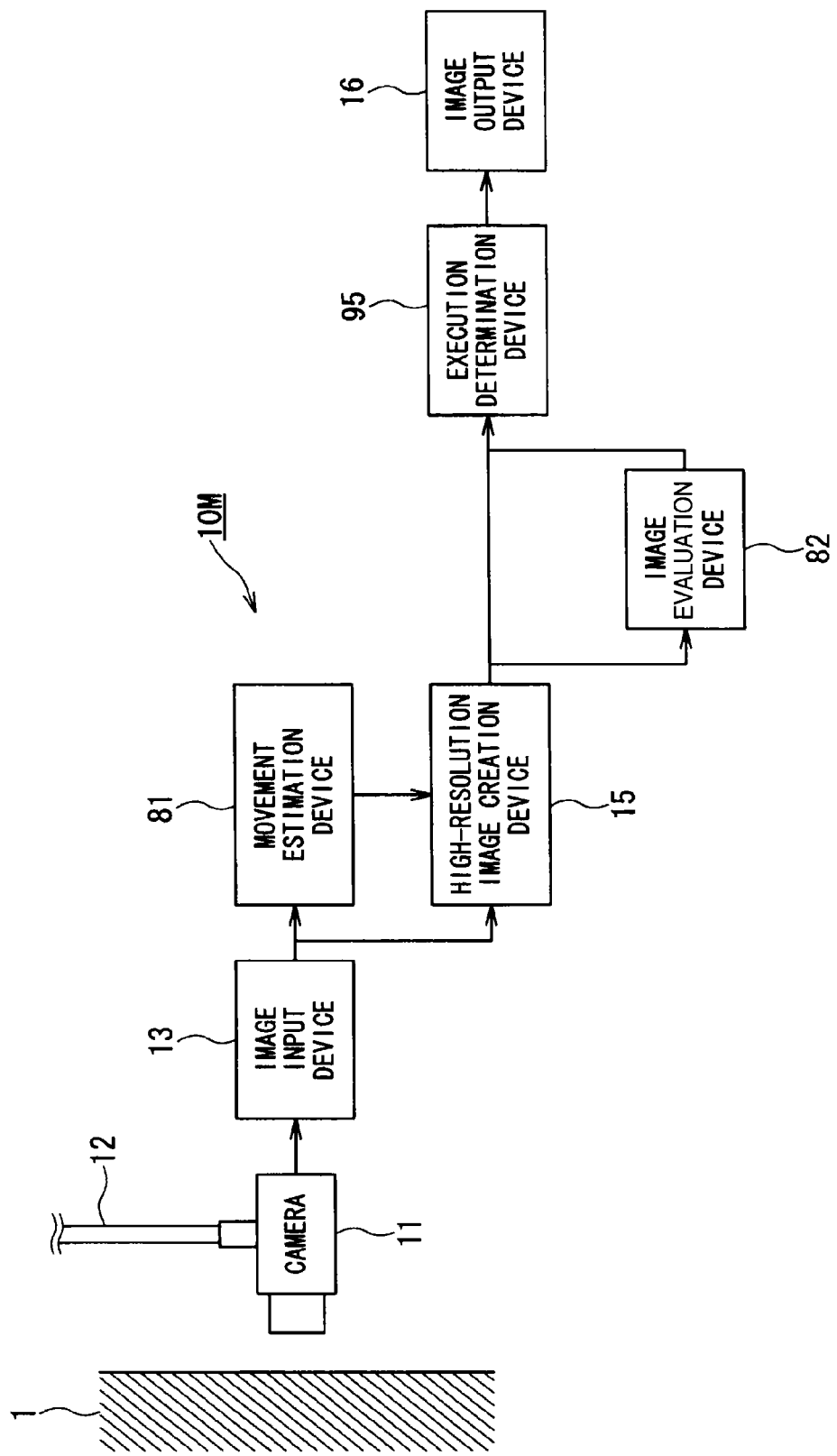
FIG. 25 is a block diagram illustrating a configuration of a visual inspection apparatus according to a thirteenth embodiment of the present invention.

FIG. 25 is a block diagram illustrating a configuration of a visual inspection apparatus (which will be referred to as "thirteenth visual inspection apparatus", hereinafter) 10M according to a thirteenth embodiment of the present invention.

The thirteenth visual inspection apparatus 10M illustrated in FIG. 25 differs from the tenth visual inspection apparatus 10J illustrated in FIG. 16 in that the thirteenth visual inspection apparatus 10M further includes an execution determination device 95. The thirteenth visual inspection apparatus 10M is not substantially different from the tenth visual inspection apparatus 10J in the other points. In light of this point, the present invention will be described by focusing on the execution determination device 95.

Based on the evaluation results of the image evaluation device 82, the execution determination device 95 determines whether or not the inspection of the inspection target 1 is to be executed. That is, the high resolution image creation device 15 outputs the generated high resolution image and the image used to generate the high resolution image to the execution determination device 95. Further, the image evaluation device 82 outputs the evaluated quality of the high resolution image to the execution determination device 95. Furthermore, the execution determination device 95 determines whether or not the inspection of the inspection target 1 is to be executed in accordance with the evaluation results of the quality of the high resolution image evaluated by the image evaluation device 82.

As the method of determining whether or not to execute inspection, a threshold is provided for the quality of a high resolution image, and the threshold is used as the criteria to determine whether or not to execute the inspection of the inspection target 1. If the quality of a high resolution image is equal to or greater than the threshold, indicating that the inspection can be executed, the execution determination device 95 outputs the high resolution image to the image output device 16. If the quality of the high resolution image is less than the threshold, indicating that the inspection cannot be executed, the execution determination device 95 outputs an inspection execution disable message to the image output device 16 as well as stops outputting the high resolution image to the image output device 16 or outputs the camera image from the image input device 13 to the image output device 16.

According to the thirteenth embodiment of the present invention, in addition to the advantages (1) and (2) obtained by the tenth embodiment, the following effect (5) is obtained.

(5) Based on the evaluation results of the quality of the high resolution image evaluated by the image evaluation device 82, the execution determination device 95 determines whether or not the inspection of the inspection target 1 is to be executed and presents the inspector with the determination results. For example, if the quality of the high resolution image is low (less than the threshold), the inspection of the inspection target 1 is cancelled and thus the reliability of the inspection of the inspection target 1 using the high resolution image can be surely guaranteed.

INDUSTRIAL APPLICABILITY

The present invention can improve the reliability of inspection by use of a high resolution image as well as can reduce the inspection time, and further can guarantee the reliability of the inspection using a high resolution image.

The invention claimed is:

1. A visual inspection apparatus, comprising:
an image input device which feeds a video image of an inspection target and outputs a digital data image;
an image selection device which selects an inspection image to be used for inspection based on a feature quantity of images outputted from the image input device;
a high resolution image creation device which generates a high resolution image having a higher resolution than the resolution of the inspection image from the inspection image by performing image alignment of a plurality of selected inspection images and estimating brightness of the high resolution image; and
an image output device which displays the inspection image and the high resolution image;
wherein the image selection device selects the inspection image to be used for inspection on the basis of both of a camera movement amount between continuous images and a lighting change state between continuous images;

an image evaluation device which evaluates the quality of the high resolution image generated by the high resolution image creation device;
wherein the image evaluation device evaluates the quality of the high resolution image in such a manner that the image evaluation device sets a local range to each of the high resolution image generated by the high resolution image creation device and the camera image obtained by performing digital processing on the video image taken by the camera, calculates the brightness dispersion of each of the local ranges, and compares between the brightness dispersion of the camera image and the brightness dispersion of the high resolution image.

2. A visual inspection apparatus, comprising:
an image input device which feeds a video image of an inspection target and outputs a digital data image;
an image selection device which selects an inspection image to be used for inspection based on a feature quantity of images outputted from the image input device;
a high resolution image creation device which generates a high resolution image having a higher resolution than the resolution of the inspection image from the inspection image by performing image alignment of a plurality of selected inspection images and estimating brightness of the high resolution image; and
an image output device which displays the inspection image and the high resolution image;
wherein the image selection device selects the inspection image to be used for inspection on the basis of both of a camera movement amount between continuous images and a lighting change state between continuous images;
an image evaluation device which evaluates the quality of the high resolution image generated by the high resolution image creation device;
wherein the image evaluation device evaluates the quality of the high resolution image in such a manner that the image evaluation device generates a converted image by inversely converting the high resolution image generated by the high resolution image creation device to an image having the same resolution as resolution of the camera image obtained by performing digital processing on the video image taken by the camera and compares between the converted image and the camera image.

3. A visual inspection apparatus, comprising:
an image input device which feeds a video image of an inspection target and outputs a digital data image;
an image selection device which selects an inspection image to be used for inspection based on a feature quantity of images outputted from the image input device;
a high resolution image creation device which generates a high resolution image having a higher resolution than the resolution of the inspection image from the inspection image by performing image alignment of a plurality of selected inspection images and estimating brightness of the high resolution image; and
an image output device which displays the inspection image and the high resolution image;
wherein the image selection device selects the inspection image to be used for inspection on the basis of both of a camera movement amount between continuous images and a lighting change state between continuous images;
an image evaluation device which evaluates the quality of the high resolution image generated by the high resolution image creation device;
a projection device which projects a light pattern onto the inspection target,
wherein the image evaluation device compares between a known size of the light pattern which the projection device projects onto the inspection target and a size of the light pattern extracted from the high resolution image generated by the high resolution image creation device to obtain a measurement accuracy and evaluates the quality of the high resolution image based on the measurement accuracy obtained by measurement from the high resolution image.

4. A visual inspection apparatus, comprising:
an image input device which feeds a video image of an inspection target and outputs a digital data image;
an image selection device which selects an inspection image to be used for inspection based on a feature quantity of images outputted from the image input device;
a high resolution image creation device which generates a high resolution image having a higher resolution than the resolution of the inspection image from the inspection image by performing image alignment of a plurality of selected inspection images and estimating brightness of the high resolution image; and
an image output device which displays the inspection image and the high resolution image;
wherein the image selection device selects the inspection image to be used for inspection on the basis of both of a camera movement amount between continuous images and a lighting change state between continuous images;
an image evaluation device which evaluates the quality of the high resolution image generated by the high resolution image creation device;
a test piece of a known size provided near the inspection target,
wherein the image evaluation device uses the test piece so as to compare between the known size of the test piece and a size obtained by measurement from the high resolution image generated by the high resolution image creation device and evaluates the quality of the high resolution image based on the measurement accuracy obtained by a result of comparing the known size and the size obtained by measurement.

5. A visual inspection apparatus, comprising:
a camera which takes an image of an inspection target;
a movement estimation device which estimates movement of the camera or the inspection target by block matching based on brightness dispersion of two images taken by the camera;
a high resolution image creation device which generates a high resolution image, having a higher resolution than the pixel resolution of a video image taken by the camera, based on the video image taken by the camera;
an image evaluation device which evaluates the quality of the high resolution image generated by the high resolution image creation device by respectively setting local ranges with respect to the camera image outputted from the image input device and the high resolution image generated by the high resolution image creation device based on the movement of the camera or the inspection target estimated by the movement estimation device, calculating a brightness dispersion of the local ranges, and evaluating the quality of the high resolution image on the basis of the brightness dispersion of the local ranges; and
an image output device which presents an inspector who visually inspects the inspection target with the high resolution image together with the quality evaluation result of the high resolution image;

wherein the movement estimation device estimates a position of the movement of any one of the camera and the inspection target in such a manner that the movement estimation device obtains an old image and a new image from a plurality of camera images obtained by performing digital processing on each of a plurality of video images taken by the camera, and compares the enlarged images obtained by performing expansion processing on the images by block matching based on a brightness dispersion.

6. A visual inspection apparatus, comprising:

a camera which takes an image of an inspection target;

a movement estimation device which estimates movement of the camera or the inspection target by block matching based on brightness dispersion of two images taken by the camera;

a high resolution image creation device which generates a high resolution image, having a higher resolution than the pixel resolution of a video image taken by the camera, based on the video image taken by the camera;

an image evaluation device which evaluates the quality of the high resolution image generated by the high resolution image creation device by respectively setting local ranges with respect to the camera image outputted from the image input device and the high resolution image generated by the high resolution image creation device based on the movement of the camera or the inspection target estimated by the movement estimation device, calculating a brightness dispersion of the local ranges, and evaluating the quality of the high resolution image on the basis of the brightness dispersion of the local ranges; and an image output device which presents an inspector who visually inspects the inspection target with the high resolution image together with the quality evaluation result of the high resolution image;

wherein the high resolution image creation device determines pixel brightness of the high resolution image in such a manner that the high resolution image creation device calculates the pixel brightness of the high resolution image as an average value of pixel intensities of a plurality of camera images used to generate the high resolution image and adds the difference in pixel brightness of a central range including the pixels of the high resolution image and a peripheral range including the central range to the average value.

* * * * *